(12) United States Patent
Mastronardi

(10) Patent No.: US 9,259,409 B2
(45) Date of Patent: Feb. 16, 2016

(54) COMPOSITIONS COMPRISING A PROSTAGLANDIN FOR TREATING NEUROPSYCHIATRIC CONDITIONS

(75) Inventor: Fabrizio G. Mastronardi, Maple (CA)

(73) Assignee: Inceptum Research & Therapeutics, Inc., Richmond Hill (CA)

( * ) Notice: Subject to any disclaimer, the term of this patent is extended or adjusted under 35 U.S.C. 154(b) by 94 days.

(21) Appl. No.: 13/981,360

(22) PCT Filed: Jan. 24, 2012

(86) PCT No.: PCT/CA2012/050037
§ 371 (c)(1),
(2), (4) Date: Jul. 30, 2013

(87) PCT Pub. No.: WO2012/100347
PCT Pub. Date: Aug. 2, 2012

(65) Prior Publication Data
US 2013/0309330 A1 Nov. 21, 2013

Related U.S. Application Data

(60) Provisional application No. 61/435,546, filed on Jan. 24, 2011.

(51) Int. Cl.
| *A01N 37/08* | (2006.01) |
| *A61K 31/215* | (2006.01) |
| *A01N 37/34* | (2006.01) |
| *A61K 31/275* | (2006.01) |
| *A61K 31/216* | (2006.01) |
| *A61K 31/165* | (2006.01) |
| *A61K 45/06* | (2006.01) |
| *C07C 405/00* | (2006.01) |
| *A61K 31/16* | (2006.01) |
| *A61K 31/4196* | (2006.01) |
| *A61K 31/4412* | (2006.01) |
| *A61K 31/4706* | (2006.01) |
| *A61K 31/53* | (2006.01) |
| *A61K 31/5575* | (2006.01) |

(52) U.S. Cl.
CPC .............. *A61K 31/216* (2013.01); *A61K 31/16* (2013.01); *A61K 31/165* (2013.01); *A61K 31/4196* (2013.01); *A61K 31/4412* (2013.01); *A61K 31/4706* (2013.01); *A61K 31/53* (2013.01); *A61K 31/5575* (2013.01); *A61K 45/06* (2013.01); *C07C 405/00* (2013.01)

(58) Field of Classification Search
CPC .......................... C07C 405/00; A61K 31/5575
USPC ................................................ 514/530, 528
See application file for complete search history.

(56) References Cited

U.S. PATENT DOCUMENTS

| 2003/0018079 A1 | 1/2003 | Richardson et al. |
| 2003/0181354 A1* | 9/2003 | Abdulrazik ............ A61K 31/00 514/1 |
| 2006/0058394 A1 | 3/2006 | Narumiya et al. |
| 2006/0194880 A1 | 8/2006 | Ueno |
| 2008/0221184 A1 | 9/2008 | Yokoyama |
| 2008/0300292 A1 | 12/2008 | Letts et al. |
| 2009/0062561 A1 | 3/2009 | Czarnik |

FOREIGN PATENT DOCUMENTS

| CA | 2279651 A1 | 3/1998 |
| CA | 2321257 A1 | 8/1999 |
| CN | 1522699 A | 8/2004 |
| CN | 101176735 A | 5/2008 |
| EP | 1386611 A1 | 2/2004 |
| GB | 2368793 A | 5/2002 |

OTHER PUBLICATIONS

NIH: Bipolar Disorder article obtained via www.nimh.nih.gov (online Feb. 27, 2015).*
Mayo Clinic: Bipolar Disorder article obtained via www.mayoclinic.org (online Feb. 27, 2015).*
Supplementary European Search Report for European Patent Application No. 12739892.3, dated Jul. 2, 2014 (8 pages).
Arnaud et al., "Proteasome-caspase-cathepsin sequence leading to tau pathology induced by prostaglandin J2 in neuronal cells," J Neurochem. 110(1):328-42 (2009).
Carrasco et al., "Prostaglandin receptor EP2 protects dopaminergic neurons against 6-OHDA-mediated low oxidative stress," Neurosci Lett. 441(1):44-9 (2008).
Gould et al., "Glycogen synthase kinase-3: a putative molecular target for lithium mimetic drugs," Neuropsychopharmacology. 30(7):1223-37 (2005).
Koh et al., "15-Deoxy-delta12,14-prostaglandin J2, a neuroprotectant or a neurotoxicant?" Toxicology. 216(2-3):232-43 (2005).
Liang et al., "Function of COX-2 and prostaglandins in neurological disease," J Mol Neurosci. 33(1):94-9 (2007). (Abstract Only).
Shao et al., "Prostaglandin E2 Stimulates the beta-catenin/T cell factor-dependent transcription in colon cancer," J Biol Chem. 280(28):26565-72 (2005).
Schweitzer et al., "A case of melancholic depression induced by beta-blocker antiglaucoma agents," Med J Aust. 189(7):406-7 (2008).

(Continued)

*Primary Examiner* — Sue Liu
*Assistant Examiner* — Helen Chui
(74) *Attorney, Agent, or Firm* — Clark & Elbing LLP; Kristina Bieker-Brady

(57) ABSTRACT

The present invention relates to methods and compositions for the treatment of neuropsychiatric conditions (e.g., bipolar disorder) by administration of prostaglandin or prostaglandin derivatives (e.g., latanoprost) to a subject (e.g., a human).

14 Claims, 12 Drawing Sheets

(56) References Cited

OTHER PUBLICATIONS

Xia et al., "Prostaglandin promotion of osteocyte gap junction function through transcriptional regulation of connexin 43 by glycogen synthase kinase 3/beta-catenin signaling," Mol Cell Biol. 30(1):206-19 (2010).

International Search Report of International Patent Application No. PCT/CA2012/050037, mailed May 1, 2012 (8 pages).

* cited by examiner

COMPOSITIONS COMPRISING A PROSTAGLANDIN FOR TREATING NEUROPSYCHIATRIC CONDITIONS

CROSS-REFERENCE TO RELATED APPLICATION

This application is the U.S. national stage filing under 35 U.S.C. §371 of International Application No. PCT/CA2012/050037, filed Jan. 24, 2012, which claims the benefit of the filing date of U.S. Provisional Application No. 61/435,546, filed Jan. 24, 2011.

BACKGROUND OF THE INVENTION

Neuropsychiatric conditions are characterized by a variety of debilitating cognitive and behavioral impairments including, but not limited to, psychotic, cognitive, anxiety, and attention disorders. In bipolar disorder, one of the most common psychotic disorders worldwide, individuals suffer from cyclic episodes of major depression and mania. Bipolar disorder affects more than 5.7 million adults each year in the United States alone, with approximately 3% of the U.S. population being diagnosed with the disorder.

Currently, lithium carbonate remains a first-line therapeutic for the treatment of bipolar disorder. Lithium functions to normalize the mood of manic individuals by inhibiting glycogen synthase kinase-3 (GSK-3) function. Despite the therapeutic properties of lithium, a number of issues detract from its therapeutic utility. For example, lithium typically takes 1 to 2 weeks before any therapeutic effects are observed and side-effects of lithium treatment include polyuria-polydipsia syndrome, structural lesions in the kidney, tremor, weight gain, diarrhea, and skin rash.

Therefore, there is an unmet need in the field to develop effective alternative therapies for the treatment of neuropsychiatric conditions, especially bipolar disorder.

SUMMARY OF THE INVENTION

The present invention provides methods and compositions for the treatment of neuropsychiatric conditions, such as bipolar disorder.

In a first aspect, the invention features a method of treating a subject having a neuropsychiatric condition by administering to the subject a therapeutically effective amount of a pharmaceutical composition containing a prostaglandin, derivative thereof, or pharmaceutically acceptable salt thereof, with or without an additional therapeutic agent.

In one embodiment of the first aspect, the prostaglandin, derivative thereof, or pharmaceutically acceptable salt thereof, is administered in an amount sufficient to inhibit glycogen synthase kinase-3 (GSK-3) in the subject. In another embodiment of the first aspect, the prostaglandin, derivative thereof, or pharmaceutically acceptable salt thereof, is administered in an amount sufficient to produce a steady state plasma concentration of prostaglandin, or derivative thereof, of from about 1 pg/ml to about 10 ng/ml (e.g., from about 1 pg/ml to about 500 pg/ml, from about 500 pg/ml to about 1 ng/ml, or from about 1 ng/ml to about 10 ng/ml). In another embodiment of the first aspect, the prostaglandin, derivative thereof, or pharmaceutically acceptable salt thereof, is deuterium-enriched. In yet another embodiment of the first aspect, the prostaglandin, or derivative thereof, is nitrosylated.

In particular embodiments of the methods of the invention, the prostaglandin, or derivative thereof, is propan-2-yl-(Z)-7-[(1R,2R,3R,5S)-3,5-dihydroxy-2-[(3R)-3-hydroxy-5-phenylpentyl]cyclopentyl]-hept-5-enoate (latanoprost), propan-2-yl-(Z)-7-[(1R,2R,3R,5S)-3,5-dihydroxy-2-[(E,3R)-3-hydroxy-4-[3-(trifluoromethyl)phenoxy]but-1-enyl] cyclopentyl]-hept-5-enoate (travoprost), and/or (Z)-7-[(1R, 2R,3R,5S)-3,5-dihydroxy-2-[(E,3S)-3-hydroxy-5-phenylpent-1-enyl]cyclopentyl]-N-ethyl-hept-5-enamide (bimatoprost). Other suitable prostaglandins, or derivatives thereof, for use in the invention include, but are not limited to, 7-[(1R,2R,3R)-3-hydroxy-2-[(E)-(3S)-3-hydroxy-1-octenyl]-5-oxo-cyclopentyl]-heptanoic acid (PGE1), (Z)-7-[(1R, 2R,3R)-3-hydroxy-2-[(E)-(3S)-3-hydroxy-1-octenyl]-5-oxo-cyclopentyl]-hept-5-enoic acid (PGE2), (Z)-7-[(1R,2R, 3R)-3-hydroxy-2-[(1E,3S,5Z)-3-hydroxyocta-1,5-dienyl]-5-oxocyclopentyl]-hept-5-enoic acid (PGE3), (Z)-7-[(1R,2R, 5S)-5-hydroxy-2-[(E,3S)-3-hydroxyoct-1-enyl]-3-oxocyclopentyl]-hept-5-enoic acid (PGD2), 7-[(1R,2R,3R, 5S)-3,5-dihydroxy-2-[(E)-(3S)-3-hydroxy-1-octenyl]-cyclopentyl]-heptanoic acid (PGF1α), (Z)-7-[(1R,2R,3R, 5S)-3,5-dihydroxy-2-[(E)-(3S)-3-hydroxy-1-octenyl]-cyclopentyl]-5-heptenoic acid (PGF2α), (Z)-7-[(1R,2R,3R, 5S)-3,5-dihydroxy-2-[(1E,3S,5Z)-3-hydroxyocta-1,5-dienyl]cyclopentyl]-hept-5-enoic acid (PGF3α), (5Z)-5-[(3aR,4R,5R,6aS)-5-hydroxy-4-[(E,3S)-3-hydroxyoct-1-enyl]-3,3a,4,5,6,6a-hexahydrocyclopenta[b]furan-2-ylidene]-pentanoic acid (PGI2/prostacyclin), (Z)-7-[(1R,2R, 3R,5S)-3,5-dihydroxy-2-(3-oxodecyl)cyclopentyl]-hept-5-enoic acid (unoprostone), (Z)-7-[(1R,2R,3R,5S)-3,5-dihydroxy-2-[(E,3R)-3-hydroxy-4-[3-(trifluoromethyl) phenoxy]but-1-enyl]cyclopentyl]-hept-5-enoic acid (fluprostenol), (Z)-7-[(1R,3R)-2-[(E,3R)-3-hydroxy-4,4-dimethyloct-1-enyl]-3-methyl-5-oxocyclopentyl]-hept-5-enoic acid (trimoprostil), (2R,3R,4R)-4-hydroxy-2-(7-hydroxyheptyl)-3-[(E)-4-hydroxy-4-methyloct-1-enyl]-cyclopentan-1-one (rioprostil), (Z)-7-[(1R,3R,5S)-2-[(E, 3R)-4-(3-chlorophenoxy)-3-hydroxybut-1-enyl]-3,5-dihydroxycyclopentyl]-hept-5-enoic acid (cloprostenol), (Z)-7-[(1S,2R,3R,5S)-2-[(2S)-3-(3-chlorophenoxy)-2-hydroxypropyl]sulfanyl-3,5-dihydroxycyclopentyl]-hept-5-enoic acid (luprostiol), (Z)-7-[(2R)-3,5-dihydroxy-2-[(E)-2-[2-(phenoxymethyl)-1,3-dioxolan-2-yl]ethenyl] cyclopentyl]-hept-5-enoic acid (etiproston), (E)-7-[3,5-dihydroxy-2-[(E)-3-hydroxy-4-thiophen-3-yloxybut-1-enyl] cyclopentyl]-hept-5-enoic acid (tiaprost), propan-2-yl-(Z)-7-[(1R,2R,3R,5S)-3,5-dihydroxy-2-(3-oxodecyl)cyclopentyl]-hept-5-enoate (isopropyl unoprostone), methyl-7-[(1R,2R, 3R)-3-hydroxy-2-[(E)-4-hydroxy-4-methyloct-1-enyl]-5-oxocyclopentyl]-heptanoate (misoprostol), (Z)-7-[(1R,2R, 3R)-3-hydroxy-2-[(E,3R)-3-hydroxy-4-(phenoxy)but-1-enyl]-5-oxocyclopentyl]-N-methylsulfonylhept-5-enamide (sulprostone), methyl(E)-7-[(1R,2R,3R)-3-hydroxy-2-[(E, 3S)-3-hydroxy-4,4-dimethyloct-1-enyl]-5-oxocyclopentyl] hept-2-enoate (gemeprost), methyl (Z)-7-[(1R,3R,5S)-2-[(3S)-5-cyclohexyl-3-hydroxypent-1-ynyl]-3,5-dihydroxycyclopentyl]hept-5-enoate (alfaprostol), and/or methyl (2Z,5Z)-7-[(2R)-2-[(E,3R)-4-(3-chlorophenoxy)-3-hydroxybut-1-enyl]-3,5-dihydroxycyclopentyl]hepta-2,5-dienoate (delprostenate).

In certain embodiments of the methods of the invention, the prostaglandin, or derivative thereof, is selected from latanoprost, travoprost, and/or bimatoprost formulated as part of a pharmaceutical composition containing prostaglandin, or derivative thereof, at a concentration of from about 0.00001% to about 0.2% (w/v) (e.g., from about 0.00001% to about 0.0001%, from about 0.0001% to about 0.001%, from about 0.001% to about 0.01%, from about 0.01% to about 0.1%, or from about 0.1% to about 0.2%). In more preferred embodiments, latanoprost and/or travoprost are present in the pharmaceutical composition at a concentration of from about 0.0001% to about 0.2% (w/v), more preferably from about 0.001% to about 0.2% (w/v), and most preferably from about 0.001% to about 0.02% (w/v). In other preferred embodiments, bimatoprost is present in the pharmaceutical composition at a concentration of from about 0.0001% to about 0.2% (w/v), more preferably from about 0.001% to about 0.2% (w/v), and most preferably from about 0.01% to about 0.2%.

In other embodiments of the methods of the invention, the pharmaceutical composition is administered for a time and in an amount sufficient such that the circulating plasma concentration of latanoprost, travoprost, and/or bimatoprost in the subject is from about 1 pg/ml to about 10 ng/ml. In more preferred embodiments, latanoprost, travoprost, and/or bimatoprost is present in the plasma of the subject at a concentration of from about 1 pg/ml to about 500 pg/ml, from about 500 pg/ml to about 1 ng/ml, or from about 1 ng/ml to about 10 ng/ml.

In still other embodiments of the methods of the invention, the method further includes administering an additional therapeutic agent, each administered in an amount that together is effective for the treatment of a neuropsychiatric condition. The prostaglandin, derivative thereof, or pharmaceutically acceptable salt thereof, and additional therapeutic agent, may be administered and formulated together, or in separate compositions or dosage forms and administered simultaneously, within 1 hour, 4 hours, 8 hours, 1 day, 2 days, 3 days, or one week of each other.

For example, the additional therapeutic agent can be an anxiolytic, antipsychotic, antidepressant, neuroleptic, tranquilizer, melatonin agonist, melatonin antagonist, melatonergic agent, benzodiazepine, barbiturate, 5-hydroxtryptamine (5-HT) antagonist, monoamine oxidase inhibitor, lithium, valproic acid, sodium valproate, lamotrigine, carbamazepine, gabapentin, topiramate, selective serotonin reuptake inhibitor (SSRI), specific monoamine reuptake inhibitor, anticholinergic, catechol-O-methyl transferase (COMT) inhibitor, monoamine oxidase-B (MOA-B) inhibitor, antioxidant, $A_{2A}$ adenosine receptor antagonist, cholinergic agonist, serotonin receptor antagonist, dopamine receptor agonist, antiepileptic, anti-Alzheimer's agent, beta-secretase (BACE) inhibitor, gamma-secretase inhibitor, 3-hydroxy-3-methylglutaryl-coenzyme A (HMG-CoA) reductase inhibitor, nonsteroidal anti-inflammatory drug (NSAID), and/or a 5-HT1A receptor agonist or partial agonist. In one particular embodiment of the methods of the invention, the prostaglandin, derivative thereof, or pharmaceutically acceptable salt thereof, and the additional therapeutic agent are formulated and administered together as a single pharmaceutical composition.

In another aspect, the invention features compositions including a therapeutically effective amount of a prostaglandin, derivative thereof, or pharmaceutically acceptable salt thereof, and an additional therapeutic agent. In one embodiment of the second aspect, the prostaglandin, derivative thereof, or pharmaceutically acceptable salt thereof, is deuterium-enriched. In another embodiment of the second aspect, the prostaglandin, or derivative thereof, is nitrosylated. The compositions of the present invention may be administered intramuscularly, intravenously, intradermally, intraarterially, intraperitoneally, intralesionally, intracranially, intraarticularly, intraprostatically, intrapleurally, intratracheally, intranasally, intravitreally, intravaginally, intrarectally, topically, intratumorally, peritoneally, subcutaneously, subconjunctivally, intravesicularlly, mucosally, intrapericardially, intraumbilically, intraocularally, orally, topically, locally, by inhalation, injection, infusion, continuous infusion, localized perfusion bathing target cells directly, catheter, lavage, in cremes, or lipid compositions.

In another aspect, the invention features a kit including packaging and a pharmaceutical composition including a prostaglandin, derivative thereof, or pharmaceutically acceptable salt thereof, that inhibits GSK-3, discussed above, and labeling to indicate that the composition is useful to treat a neuropsychiatric condition.

The prostaglandin, or a derivative or analog thereof, and/or additional therapeutic agent may be optionally administered as a pharmaceutically acceptable salt, such as a non-toxic acid addition salt, metal salt (e.g., sodium, potassium, magnesium, or calcium salt), or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, and trifluoroacetic acids, among others; polymeric acids such as tannic acid, and carboxymethyl cellulose, among others; and inorganic acid such as hydrochloric acid, hydrobromic acid, sulfuric acid, and phosphoric acid, among others. Metal complexes include calcium, zinc, and iron, among others.

The methods and compositions of the invention may be used to treat any of a wide variety of neuropsychiatric conditions that are characterized psychotic, cognitive, anxiety, or attention disorders. Psychotic disorders include bipolar disorder, schizophrenia, schizophreniform disorder, schizoaffective disorder, delusional disorder, drug-induced psychotic disorder, depression, sundowners syndrome due to Alzheimer's disease or other dementia, and post-traumatic stress disorder. Cognitive disorders include amnestic disorder, age-related cognitive decline, and dementia associated a neuroinflammatory condition, which includes multiple sclerosis (MS), human immunodeficiency virus (HIV)-associated dementia, autism, Huntington's disease, Pick's disease, Creutzfeldt-Jakob disease, stroke, amylotrophic lateral sclerosis (ALS), Alzheimer's disease, Parkinson's disease, or ischemic injury. Anxiety disorders include generalized anxiety disorder, obsessive compulsive disorder, social phobia, panic attack, premenstrual syndrome, and premenstrual dysphoric disorder. Attention disorders include attention deficit hyperactivity disorder, Tourette's syndrome, eating disorder, and autism.

The methods and compositions of the invention are particularly suitable for treating bipolar disorder, including bipolar I disorder, bipolar II disorder, cyclothymia, mixed bipolar disorder, rapid-cycling bipolar disorder, hypomania, dysthymia, and/or acute mania. In a most preferred embodiment, latanoprost, or a derivative thereof, is used to treat a subject having bipolar disorder. Other preferred prostaglandin, or prostaglandin derivatives, useful in treating a subject with bipolar disorder include travoprost or bimatoprost, or a derivative thereof.

Typically, the subject is a mammal, such as a human.

DEFINITIONS

An "anxiety disorder" herein is meant any pathologic anxiety condition and includes different forms of abnormal, pathological anxiety, fears, phobias, and nervous conditions that are described as irrational or illogical worry that is not based on fact. Anxiety disorders cover a wide range of severities from social anxieties to panic disorders, including, but not limited to, generalized anxiety disorder, obsessive compulsive disorder, post traumatic stress disorder (PTSD), agoraphobia, specific phobia, acute stress disorder, social phobia, panic attack, premenstrual syndrome, and premenstrual dysphoric disorder.

By "attention disorder" is herein meant any disease, disorder, or condition involving an impaired ability to concentrate on selected features of the environment to the relative exclusion of others. Attention disorders include, but are not limited to, attention deficit hyperactivity disorder (ADHD) or a related disorder, Tourette's syndrome, eating disorder, and autism. ADHD and related disorders are disorders characterized by developmentally inappropriate degrees of inattention, overactivity, and impulsivity, such as Attention Deficit Hyperactivity Disorder—combined subtype, Attention Deficit Hyperactivity Disorder—predominantly hyperactive-impulsive subtype, Attention Deficit Hyperactivity Disorder—predominantly inattentive subtype, Attention Deficit Disorder with or without hyperactivity, Hyperkinetic Disorder, oppositional defiant disorder and conduct disorder. Attention Deficit Hyperactivity Disorder is a disorder characterized by inattention, impulsiveness, and hyperactivity. This disorder can impair social function, learning and/or development and is therefore now recognized as a serious problem. It is further recognized that many children with ADHD go on to develop other comorbid conditions or social problems in adulthood. In clinical terms ADHD is diagnosed if any one of the three main clinical features, inattention, over-activity, and impulsiveness, persists in two or more situations, e.g., in both a home and school environment (American Psychiatric Association. Diagnostic and Statistical Manual of Mental Disorders, Fourth Edition (DSM-IV) Washington D.C.; American Psychiatric Association, 1994). A diagnosis of Hyperkinetic Disorder is made only if all three of the main clinical features (inattention, over-activity and impulsiveness) have been present from an early age, persist in more than one situation (e.g., home and school) and impair function (The ICD-10 Classification of Mental and Behavioural Disorders: Diagnostic Criteria for Research. Geneva: World Health Organisation, 1993: 155-7). The methods of the invention can be useful for the treatment of an attention disorder.

By "bipolar disorder" or "manic-depressive disorder" is herein meant a psychiatric condition common across cultures and age groups, which causes shifts in an individual's mood, energy, and ability to function. Bipolar disorder can include cyclic episodes of mania and depression, or only mania. Bipolar disorder can be further divided into bipolar I disorder, bipolar II disorder, cyclothymia, mixed bipolar disorder, rapid-cycling bipolar disorder, hypomania, dysthymia, and acute mania, each of which can be treated using the methods of the invention. The symptoms of bipolar disorder can be severe enough to require clinical intervention (see, e.g., DSM-IV, American Psychiatric Association, Washington, D.C., USA, 1997).

As used herein, the term "cognitive disorder" refers to any chronic condition that impairs reasoning ability. Cognitive disorders include, but are not limited to, amnestic disorder, age-related cognitive decline, and dementia associated with a neuroinflammatory condition (e.g., Alzheimer's disease, multiple sclerosis, Parkinson's disease).

As used herein, the term "derivative" or "analog" refers to derivatives and analogs of prostaglandins, including prostaglandin prodrugs (e.g., esters or amides), deuterium-enriched prostaglandins, and nitrosylated prostaglandins. Derivatives and analogs of prostaglandins are either capable of inhibiting GSK-3 or serve as "prodrugs" converted in vivo into a biologically active compound capable of inhibiting GSK-3. Examples of prostaglandin derivatives and analogs include, without limitation, latanoprost, travoprost, and bimatoprost.

As used herein, the term "deuterium-enriched" refers to prostaglandins or prostaglandin derivatives and analogs with a level of deuterium (D or $^2$H) that has been enriched to be greater than 0.015%, the natural abundance of deuterium. Deuterium-enriched prostaglandins are described, for example, in U.S. Pub. No. 2009/0062561, which is incorporated herein by reference in its entirety. Deuterium-enriched prostaglandins or prostaglandin-derivatives include, for example, deuterium-enriched latanoprost.

The term "glycogen synthase kinase-3" or "GSK-3" herein refers to a kinase enzyme of either GSK-3$\alpha$ or GSK-3$\beta$ isoform.

The term "inhibit" or its grammatical equivalent, such as "inhibiting," is not intended to require complete reduction in biological activity of a target (e.g., GSK-3). Such reduction is preferably by at least about 50%, at least about 75%, at least about 90%, and more preferably by at least about 95% of the activity of the molecule in the absence of the inhibitory effect, e.g., in the absence of an inhibitor (e.g., a prostaglandin or prostaglandin derivative or analog, e.g., latanoprost). More preferably, the term refers to an observable or measurable reduction in activity. In treatment scenarios, preferably the inhibition is required to produce a therapeutic benefit in the condition being treated (e.g., a neuropsychiatric condition, e.g., bipolar disorder).

By "neuroinflammatory condition" as used herein refers to a clinical neurologic problem characterized by the presence of inflammation in the brain. Examples of such disorders include multiple sclerosis (MS), cerebrovascular conditions including stroke, human immunodeficiency virus (HIV)-associated dementia, certain forms of chronic pain, autism, Huntington's disease, Pick's disease, Creutzfeldt-Jakob disease, amylotrophic lateral sclerosis (ALS), Alzheimer's disease, Parkinson's disease, and ischemic injury such as traumatic brain injury (TBI).

The term "neuropsychiatric condition" as used herein refers to clinical problems of cognition and/or behavior caused by an injury, disease, or disorder associated with the brain. Neuropsychiatric conditions include, but are not limited to, psychotic disorders, cognitive disorders, anxiety disorders, and attention disorders.

As used herein, the term "nitrosylated" refers to prostaglandin derivatives and analogs bearing one or more nitrosyl moieties. Nitrosylated prostaglandins are described, for example, in U.S. Pat. Nos. 7,176,238 and 7,910,767 and U.S. Pub. No. 2008/0300292, each of which is incorporated herein by reference in its entirety.

A "pharmaceutically acceptable carrier" is meant a carrier which is physiologically acceptable to a treated mammal (e.g., a human) while retaining the therapeutic properties of the compound with which it is administered. One exemplary pharmaceutically acceptable carrier is physiological saline. Other physiologically acceptable carriers and their formulations are known to one skilled in the art and described, for example, in Remington's Pharmaceutical Sciences (18$^{th}$ edition, A. Gennaro, 1990, Mack Publishing Company, Easton, Pa.), incorporated herein by reference.

The term "prostaglandin" or "PG" refers to a group of compounds which may be derived from arachidonic acid by the action of cyclooxygenase. Structurally, PGs are lipid compounds having 20 carbon atoms, including a 5-carbon ring. PGs are classified according to the characteristics of the 5-carbon ring (e.g., prostaglandins A, B, C, D, E, F, J, and I) as well as by the saturation of the alpha and omega carbon chains on the ring carbons 8 and 12, (e.g., $PG_1\delta$, $PG_2\delta$, and PG$_3$δ). The classifications of prostaglandins are summarized in U.S. Pat. No. 5,151,444 (see, e.g., column 1, lines 11-65; column 2, lines 5-35). As used herein, PG includes, but is not limited to, natural and synthetic PGs.

As used herein, the term "psychotic disorder" refers to any mood or affective disorder or condition characterized by psychosis, which may involve cognitive problems, delusions, and/or hallucinations. Psychotic disorders include, but are not limited to, bipolar disorder, schizophrenia, schizophreniform disorder, schizoaffective disorder, delusional disorder, drug-induced psychotic disorder, depression, sundowners syndrome due to Alzheimer's disease or other dementia, and post-traumatic stress disorder.

As used herein, the term "steady state plasma concentration" refers to administration according to the methods of the invention in a dosing regimen that produces an average plasma concentration of prostaglandin or prostaglandin derivative in human subjects (e.g., the average over 10 subjects) of from about 1 pg/ml to about 10 ng/ml (e.g., from about 1 pg/ml to about 500 pg/ml, from about 500 pg/ml to about 1 ng/ml, or from about 1 ng/ml to about 10 ng/ml), wherein the steady state plasma concentration is the average concentration observed in plasma at 4 times the circulating half-life following administration of the prostaglandin or prostaglandin derivative.

A "subject" or "patient" is a vertebrate, such as a mammal, e.g., a human. Mammals include, but are not limited to, farm animals (such as cows), sport animals, pets (such as cats, dogs, and horses), mice, rats, and primates.

By "therapeutic agent" is meant any compound that is used in the detection, diagnosis, or treatment of a disease or condition (e.g., a neuropsychiatric condition in a human). Such compounds may be naturally occurring, modified, or synthetic. Therapeutic agents may promote or inhibit any biological process implicated in a pathway (e.g., a GSK-3-associated pathway, e.g., Wnt signaling pathway) associated with a human disease, disorder, or condition (e.g., bipolar disorder). For example, molecules that inhibit GSK-3 are described in U.S. Pat. No. 7,598,288, which is incorporated herein by reference in its entirety.

The term "therapeutically effective amount" or "effective amount" refers to a sufficient amount of an agent to provide a desired biological, therapeutic, and/or prophylactic result. That result can be reduction and/or alleviation of the signs, symptoms, or causes of a disease, disorder, or condition (e.g., a neuropsychiatric condition, e.g., bipolar disorder) or any other desired alteration of a biological system. For example, a "therapeutically effective amount" when used in reference to treating a neuropsychiatric condition refers to an amount of one or more compounds that provides a clinically significant decrease in the neuropsychiatric condition, e.g., relieves or diminishes one or more symptoms caused by a condition associated with the neuropsychiatric condition.

As used herein, and as well understood in the art, "treatment" is an approach for obtaining beneficial or desired results, such as clinical results. Beneficial or desired results can include, but are not limited to, alleviation or amelioration of one or more symptoms or conditions; diminishment of extent of disease, disorder, or condition; stabilization (i.e., not worsening) of a state of disease, disorder, or condition; prevention of spread of disease, disorder, or condition; delay or slowing the progress of the disease, disorder, or condition; amelioration or palliation of the disease, disorder, or condition; and remission (whether partial or total), whether detectable or undetectable. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment.

Other features and advantages of the invention will be apparent from the following Detailed Description, the drawings, and the claims.

BRIEF DESCRIPTION OF THE DRAWINGS

The invention may be more completely understood in consideration of the accompanying drawings, which are incorporated in and constitute a part of this specification, and together with the description, serve to illustrate several embodiments of the invention.

Figure 1A:
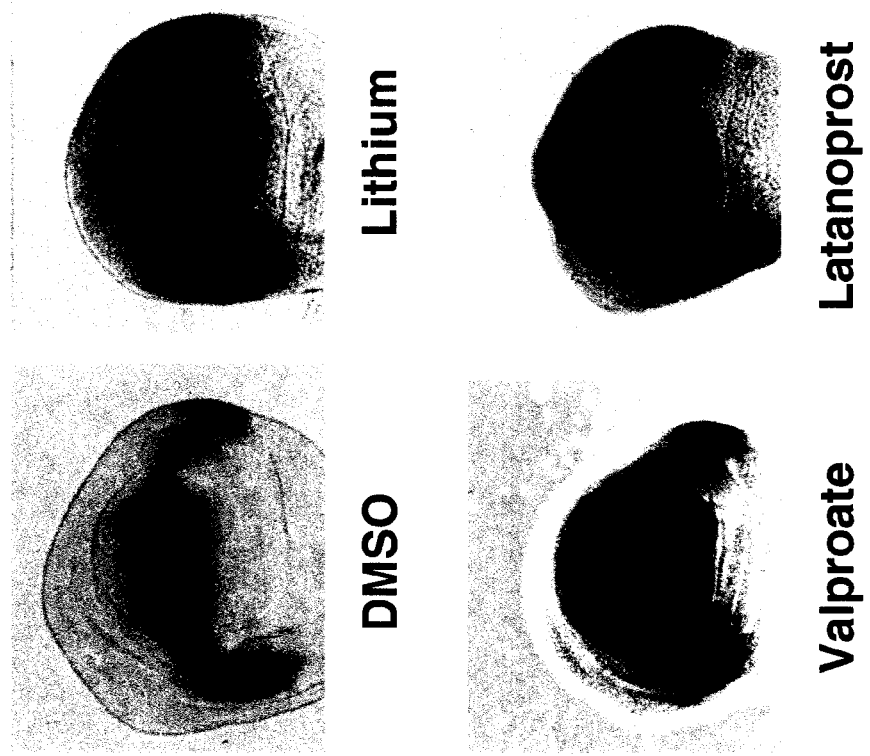
FIG. 1A is a series of compound light microscope images showing Distal-less (Dll) lacZ expression in *Drosophila* wing imaginal discs treated with DMSO vehicle, lithium (1 mM), valproate (1 mM), or latanoprost (20 µM).

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is based, at least in part, on the discovery that prostaglandin (PG) and PG-like compounds (e.g., prostaglandin F2α analogs, e.g., latanoprost) are effective in treating neuropsychiatric conditions such as bipolar disorder. Furthermore, the data presented herein show that these compounds inhibit glycogen synthase kinase-3 (GSK-3) and exhibit greater specificity in treating neuropsychiatric conditions, such as bipolar disorder, than common treatment regimens such as lithium carbonate.

Neuropsychiatric Conditions and Bipolar Disorder

The present invention provides alternative therapies for the treatment of neuropsychiatric conditions, such as bipolar disorder. The methods and compositions of the present invention make use of one or more prostaglandin, or derivative thereof, (e.g., latanoprost) in treating neuropsychiatric conditions (e.g., bipolar disorder) by inhibiting GSK-3.

Currently, numerous neuropsychiatric conditions (e.g., bipolar disorder) are commonly treated with compositions containing lithium (e.g., lithium carbonate), which also functions to normalize the mood of manic individuals by inhibiting GSK-3 function. Despite the therapeutic properties of lithium, a number of issues detract from its therapeutic utility. For example, lithium typically takes 1 to 2 weeks before any therapeutic effects are observed and side-effects of lithium treatment include polyuria-polydipsia syndrome, structural lesions in the kidney, tremor, weight gain, diarrhea, and skin rash.

The use of prostaglandins, or derivatives thereof, provides an alternative treatment for neuropsychiatric conditions by targeting GSK-3 via an alternative means. Examples of neuropsychiatric conditions, include psychotic (e.g., bipolar disorder, schizophrenia, schizophreniform disorder, schizoaffective disorder, delusional disorder, drug-induced psychotic disorder, depression, sundowners syndrome due to Alzheimer's disease or other dementia, and post-traumatic stress disorder), cognitive (e.g., amnestic disorder, age-related cognitive decline, and dementia associated with a neuroinflammatory conditions, e.g., multiple sclerosis (MS), human immunodeficiency virus (HIV)-associated dementia, autism, Huntington's disease, Pick's disease, Creutzfeldt-Jakob disease, stroke, amylotrophic lateral sclerosis (ALS), Alzheimer's disease, Parkinson's disease, and ischemic injury), anxiety (e.g., generalized anxiety disorder, obsessive compulsive disorder, social phobia, panic attack, premenstrual syndrome, and premenstrual dysphoric disorder), and attention disorders (e.g., attention deficit hyperactivity disorder, Tourette's syndrome, eating disorder, and autism).

In one embodiment, the methods and compositions of the invention are used to treat bipolar disorder, a common disease usually diagnosed in young adults. Sometimes called manic-depressive disorder, bipolar disorder causes cyclic mood swings that range from the lows of depression to the highs of mania. Physical changes may also occur, especially in severe depression. These include insomnia or hypersomnia, anorexia and/or weight loss, overeating and/or weight gain, decreased energy and libido, and disruption of normal circadian rhythms of activity, body temperature, and many endocrine functions.

The signs and symptoms of depression (or depressive episode) can include the following: lasting sad, anxious, or empty mood; feelings of hopelessness or pessimism; feelings of guilt, worthlessness, or helplessness; loss of interest or pleasure in activities once enjoyed; decreased energy, a feeling of fatigue, difficulty concentrating, remembering, or making decisions; restlessness or irritability; sleeping too much, or difficulty sleeping; change in appetite and/or unintended weight loss or gain; chronic pain or other persistent bodily symptoms that are not caused by physical illness or injury; and thoughts of death or suicide, or suicide attempts. A depressive episode is diagnosed if five or more of these symptoms last for most of the day, nearly every day, for a period of two weeks or longer.

The signs and symptoms of mania (or manic episode) can include the following: increased energy, activity, and restlessness; excessive "high," overly good, euphoric mood; extreme irritability; racing thoughts and talking very fast, jumping from one idea to another; distractibility (e.g., difficulty concentrating); decreased need for sleep; unrealistic belief in one's abilities and powers; poor judgment; spending sprees; a lasting period of behavior that is different from usual; increased sexual drive; drug abuse (e.g., cocaine, alcohol, sleep medications); and provocative, aggressive, or interfering behavior. A manic episode may be diagnosed if elevated mood occurs accompanied by three or more of the other symptoms for most of the day, at least nearly every day, for a period of one week or longer.

A mild to moderate level of mania is generally referred to as hypomania. Hypomania may feel good to the individual who experiences it and may even be associated with adequate functioning and enhanced productivity. A mild to moderate level of depression is generally referred to as dysthymia. Dysthymia is chronic and symptoms usually last for at least two years, and often for much longer. These signs may represent early behavioral changes that, without proper treatment, could become severe mania or depression.

Sometimes severe episodes of mania or depression include symptoms of psychosis. Common psychotic symptoms are hallucinations (e.g., hearing, seeing, or sensing the presence of things not actually there) and delusions (e.g., false beliefs held in the face of strong contradictory evidence). Psychotic symptoms in bipolar disorder tend to reflect the extreme mood state at the time. For example, delusions of grandiosity may occur during mania; delusions of guilt or worthlessness may appear during depression. The various mood states in bipolar disorder can be referred to as a spectrum of mood states.

Bipolar disorder can be characterized by episodic mood swings and includes bipolar I disorder, bipolar II disorder, cyclothymia, mixed bipolar disorder, rapid-cycling bipolar disorder, hypomania, dysthymia, and acute mania. In bipolar I disorder, an individual suffers from cyclic episodes of severe mania and depression. In bipolar II disorder, an individual suffers from cyclic episodes of hypomania and depression. When four or more episodes of illness occur within a 12-month period, an individual is characterized as having rapid-cycling bipolar disorder.

Glycogen Synthase Kinase-3 (GSK-3)

GSK-3 was first identified as a kinase that phosphorylates glycogen synthase but is now known to be involved in multiple signaling pathways. GSK-3 is a proline-directed serine/threonine kinase originally identified as having an activity that phosphorylates glycogen synthase. GSK-3 includes two isoforms, GSK-3α and GSK-3β, both of which are encompassed by the term "GSK-3" as used herein. The nucleic acid and protein sequences of GSK-3 are described, for instance, in Genbank ID NM 019884 (human GSK-3α), Genbank ID NM 002093 (human GSK-3β), and US Patent Application No. 2003/0163836, which are incorporated by reference for such teachings.

GSK-3 is constitutively active and only inactivated when phosphorylated at a single serine residue on its N-terminal regulatory domain. The target serines are Serine-21 and Serine-9 on GSK-3α and GSK-3β, respectively. GSK-3 can be inactivated by growth factors or hormones that signal through receptor tyrosine kinases (e.g., Wnt/Wg, insulin). The inactivation of GSK-3 is mediated by the serine/threonine kinase protein kinase B (PKB or AKT).

GSK-3, in turn, regulates downstream substrates such as microtubule-associated protein-1b (MAP-1b) and β-catenin. β-catenin is a crucial regulator of cytoskeletal organization of adherins junctions, which are associated with synaptic plasticity. GSK-3 has been shown, for instance, to phosphorylate β-catenin, targeting the transcription factor for ubiquitination and proteosomal degradation. The present invention therefore also encompasses the use of prostaglandin, or derivatives thereof, to stabilize β-catenin.

Methods of Prophylaxis or Treatment of a Neuropsychiatric Condition Using the Methods and Compositions of the Invention The methods and compositions of the invention can be used for treating a subject with a neuropsychiatric condition. In particular, the invention can be used to treat a subject with psychotic (e.g., bipolar disorder, schizophrenia, schizophreniform disorder, schizoaffective disorder, delusional disorder, drug-induced psychotic disorder, depression, sundowners syndrome due to Alzheimer's disease or other dementia, and post-traumatic stress disorder), cognitive (e.g., amnestic disorder, age-related cognitive decline, and dementia associated with a neuroinflammatory condition, e.g., multiple sclerosis (MS), human immunodeficiency virus (HIV)-associated dementia, autism, Huntington's disease, Pick's disease, Creutzfeldt-Jakob disease, stroke, amylotrophic lateral sclerosis (ALS), Alzheimer's disease, Parkinson's disease, and ischemic injury), anxiety (e.g., generalized anxiety disorder, obsessive compulsive disorder, social phobia, panic attack, premenstrual syndrome, and premenstrual dysphoric disorder), and/or attention disorders (e.g., attention deficit hyperactivity disorder, Tourette's syndrome, eating disorder, and autism).

Preferably, the invention can be used to treat a subject with bipolar disorder, including bipolar I disorder, bipolar II disorder, cyclothymia, mixed bipolar disorder, rapid-cycling bipolar disorder, hypomania, dysthymia, and acute mania.

Despite the availability of treatments for bipolar disorder (e.g., lithium, tricyclic antidepressants, monoamine oxidase inhibitors, selective serotonin reuptake inhibitors (SSRIs), specific monoamine reuptake inhibitors, 5-HT1A receptor antagonists, agonists, and partial agonists), the observed delay in therapeutic effect and numerous adverse side-effects suggest a need for alternative effective therapies.

Specifically, the present invention relates to methods of treating a subject with a neuropsychiatric condition (e.g., bipolar disorder) by administration of a prostaglandin, or derivative thereof, alone or in combination with an additional therapeutic agent (e.g., either as a single composition or separate compositions). Prostaglandins, or derivatives thereof, act to inhibit GSK-3 and/or stabilize β-catenin, thereby providing a novel and alternative treatment for neuropsychiatric conditions such as bipolar disorder.

Pharmaceutical Formulation and Administration of the Compositions of the Invention Administration The compositions of the invention can be administered to a subject (e.g., a human) to treat, prevent, ameliorate, inhibit the progression of, or reduce the severity of one or more symptoms of a neuropsychiatric condition (e.g., bipolar disorder) in the subject. Examples of the symptoms of, e.g., bipolar disorder that can be treated using the compositions of the invention include, e.g., depression, mania, psychosis, and physical changes such as weight loss or weight gain. These symptoms, and their resolution during treatment, may be measured by, e.g., a physician during a physical examination or by other tests and methods known in the art.

The compositions utilized in the methods described herein can be formulated for administration by a route selected from, e.g., parenteral, dermal, transdermal, ocular, inhalation, buccal, sublingual, perilingual, nasal, rectal, topical administration, and oral administration. Parenteral administration includes intravenous, intraperitoneal, subcutaneous, and intramuscular administration. Parenteral, intranasal, or intraocular administration may be provided by using, e.g., aqueous suspensions, isotonic saline solutions, sterile and injectable solutions containing pharmacologically compatible dispersants and/or solubilizers, for example, propylene glycol or polyethylene glycol, lyophilized powder formulations, and gel formulations. The preferred method of administration can vary depending on various factors (e.g., the components of the composition being administered and the severity of the condition being treated). Formulations suitable for oral or nasal administration may consist of liquid solutions, such as an effective amount of the composition dissolved in a diluent (e.g., water, saline, or PEG-400), capsules, sachets, tablets, or gels, each containing a predetermined amount of the composition of the invention. The pharmaceutical composition may also be an aerosol formulation for inhalation, e.g., to the bronchial passageways. Aerosol formulations may be mixed with pressurized, pharmaceutically acceptable propellants (e.g., dichlorodifluoromethane, propane, or nitrogen). In particular, administration by inhalation can be accomplished by using, e.g., an aerosol containing sorbitan trioleate or oleic acid, for example, together with trichlorofluoromethane, dichlorofluoromethane, dichlorotetrafluoroethane, or any other biologically compatible propellant gas.

Immunogenicity of the composition of the invention may be significantly improved if it is co-administered with an immunostimulatory agent or adjuvant. Suitable adjuvants well-known to those skilled in the art include, e.g., aluminum phosphate, aluminum hydroxide, QS21, Quil A (and derivatives and components thereof), calcium phosphate, calcium hydroxide, zinc hydroxide, glycolipid analogs, octodecyl esters of an amino acid, muramyl dipeptides, polyphosphazene, lipoproteins, ISCOM matrix, DC-Chol, DDA, cytokines, and other adjuvants and derivatives thereof.

Pharmaceutical compositions according to the invention described herein may be formulated to release the composition immediately upon administration (e.g., targeted delivery) or at any predetermined time period after administration using controlled or extended release formulations. Administration of the pharmaceutical composition in controlled or extended release formulations is useful where the composition, either alone or in combination, has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window at the site of release; or (iii) a short biological half-life, so that frequent dosing during a day is required in order to sustain a therapeutic level.

Many strategies can be pursued to obtain controlled or extended release in which the rate of release outweighs the rate of metabolism of the pharmaceutical composition. For example, controlled release can be obtained by the appropriate selection of formulation parameters and ingredients, including, e.g., appropriate controlled release compositions and coatings. Suitable formulations are known to those of skill in the art. Examples include single or multiple unit tablet or capsule compositions, oil solutions, suspensions, emulsions, microcapsules, microspheres, nanoparticles, patches, and liposomes.

The compositions of the invention may be administered to provide treatment to a subject having a neuropsychiatric condition, such as bipolar disorder. The composition may be administered to the subject, e.g., 1, 2, 3, 4, 5, 6, 7, 8, 9, 10, 15, 20, 30, 35, 40, 45, 50, 55, or 60 minutes, 2, 4, 6, 10, 15, or 24 hours, 2, 3, 5, or 7 days, 2, 4, 6 or 8 weeks, 3, 4, 6, or 9 months, 1, 2, 3, 4, 5, 6, 7, 8, 9, 10, 15, 20 years or longer post-diagnosis of bipolar disorder.

When treating a neuropsychiatric condition (e.g., bipolar disorder), the compositions of the invention may be administered to the subject either before the occurrence of symptoms or a definitive diagnosis or after diagnosis or symptoms become evident. For example, the composition may be administered, e.g., immediately after diagnosis or the clinical recognition of symptoms or 2, 4, 6, 10, 15, or 24 hours, 2, 3, 5, or 7 days, 2, 4, 6 or 8 weeks, or even 3, 4, or 6 months after diagnosis or detection of symptoms.

The compositions may be sterilized by conventional sterilization techniques, or may be sterile filtered. The resulting aqueous solutions may be packaged for use as is, or lyophilized, the lyophilized preparation may be administered in powder form or combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the prostaglandin(s), or derivative(s) thereof, and, if desired, one or more additional therapeutic agents, such as in a sealed package of tablets or capsules, or in a suitable dry powder inhaler (DPI) capable of administering one or more doses.

Dosages

The dose of the compositions of the invention or the number of treatments using the compositions of the invention may be increased or decreased based on the severity of, occurrence of or progression of the neuropsychiatric condition in the subject (e.g., based on the severity of one or more symptoms of, e.g., bipolar disorder), but generally range from about 0.00001% to about 0.2% (w/v) of each agent per dose one or more times per week (e.g., 2, 3, 4, 5, 6, or 7 or more times per week). Preferred dosages include from about 0.001% to about 0.02% (w/v) of latanoprost or travoprost and from about 0.01% to about 0.2% (w/v) of bimatoprost.

The pharmaceutical compositions of the invention can be administered in a therapeutically effective amount that provides a protective effect against the neuropsychiatric condition (e.g., bipolar disorder). The dosage administered depends on the subject to be treated (e.g., the age, body weight, capacity of the immune system, and general health of the subject being treated), the form of administration (e.g., as a solid or liquid), the manner of administration (e.g., by injection, inhalation, dry powder propellant), and the cells targeted (e.g., epithelial cells, such as blood vessel epithelial cells, nasal epithelial cells, or pulmonary epithelial cells). The composition is preferably administered in an amount that provides a sufficient level of prostaglandin, or derivative thereof, that reduces or prevents one or more symptoms of, e.g., bipolar disorder, without undue adverse physiological effects in the subject caused by the treatment.

In addition, single or multiple administrations of the compositions of the present invention may be given to a subject with a neuropsychiatric condition (e.g., one administration or administration two or more times). Responsiveness of subjects treated by the pharmaceutical compositions described herein may be measured by, e.g., a physician during a physical examination or by other tests and methods known in the art. The dosages may then be adjusted or repeated as necessary.

A single dose of the compositions of the invention may reduce, treat, or prevent one or more symptoms of bipolar disorder in the subject. In addition, a single dose of the compositions of the invention can also be used to achieve therapy in subjects being treated for bipolar disorder. Multiple doses (e.g., 2, 3, 4, 5, or more doses) can also be administered, in necessary, to these subjects.

Carriers, Excipients, Diluents

The compositions of the invention include prostaglandins and derivatives thereof (e.g., latanoprost). Therapeutic formulations of the compositions of the invention are prepared using standard methods known in the art by mixing the active ingredient having the desired degree of purity with optional physiologically acceptable carriers, excipients, or stabilizers (Remington's Pharmaceutical Sciences, $21^{th}$ ed., A. Gennaro, 2005, Lippincott, Williams & Wilkins, Philadelphia, Pa.). Acceptable carriers, include saline, or buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagines, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, but preferably, the formulation contains a pharmaceutically acceptable salt, preferably sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant at a concentration of 0.005 to 0.02%.

EXAMPLES

The following examples are to illustrate the invention. They are not meant to limit the invention in any way.

Example 1

Materials and Methods

The experiments described herein may be carried out using the following materials and methods.

*Drosophila* Strains and Culture

Line W1118 flies (Bloomington Stock Center, Bloomington, Ind., USA) were reared at 25° C. on standard cornmeal agar food.

Treatment During Larval Development

Stock solutions of drug compounds were formulated at concentrations of 10 mM in dimethylsulfoxide (DMSO) cell culture grade (Sigma Aldrich, St. Louis, Mo., USA). For culture of wing imaginal discs, a total of 30 third instar (72 hours after egg laying) wing imaginal discs were dissected using a fine tungsten needle. The imaginal tissues were then placed in a 1-mL solution of X medium (Davis and Shearn, Science, 196: 438-440, 1977) supplemented with treatment compound (e.g., latanoprost, PGE2, PGF2α, unoprostone, bimatoprost, fluprostenol) or DMSO vehicle control. The imaginal discs were then processed further for various experiments as described below.

Fixation and Immunological Detection in Imaginal Discs

To assay expression in Dll lacZ imaginal discs (Sullivan et al., *Drosophila* Protocols, 212, 2000), wing discs were fixed in glutaraldehyde and X-gal solution was used to assay for beta-galactosidase activity in situ. Immunofluorescence staining of discs was conducted as described (Basler and Struhl, Nature, 368: 208-214, 1994). Antibodies to Dll (Duncan et al., Genes Dev., 12: 1290-1303, 1998) and GFP (Molecular Probes Inc., Eugene, Oreg., USA), and secondary antibodies (Vector Labs, Burlington, ON, Canada) were used for labeling. Labeled imaginal discs were then placed in DAPI mounting medium (Vector Labs, Burlington, ON, Canada) and imaged using a two-photon Zeiss confocal microscope with LSM Zeiss software.

Cell Culture and Treatments

Human embryonic kidney 293T (HEK293T) cells, U87MG astrocytoma and the human oligodendrocyte cell line MO3-13 were grown in Dubelco Minimal Eagle Media (DMEM) (Invitrogen, Carlsbad, Calif., USA) supplemented with 5% heat inactivated fetal bovine serum. Cells were grown to 70% confluence prior to treatment. HEK293T cells were treated individually with 10 mM latanoprost, unoprostone, bimatoprost, fluprostenol, PGE2, and PGF2α in serum-free DMEM. Cells were exposed to drug for 3 hours at 37° C. in a 5% $CO_2$ incubator. U87MG cells were grown to 70% confluence prior to treatment. Cells were treated with either DMSO vehicle (NT) or individually with 1, 5 and 10 μM latanoprost in DMEM lacking fetal bovine serum. Cells were exposed to treatments for 6 hours at 37° C. in a 5% $CO_2$ incubator. The human oligodendrocyte cell line MO3-13 was grown and differentiated according to the methods described in McLaurin et al. (McLaurin, J., Trudel, G. C., Shaw, I. T., Antel, J. P., and Cashman, N. R., J. Neurobiol., 26: 283-293, 1995). On the third day of serum starvation, cells were treated with either DMSO vehicle (NT) or individually with 1, 5 and 10 μM latanoprost. Cells were exposed to treatments for 6 hours at 37° C. in a 5% $CO_2$ incubator.

Protein Analysis and Western Immunoblots

For detection of CREB and Serine-133 (S133)-phosphorylated CREB, serotonin receptor 5HT2A, TCF/LEF1, BDNF and TNF-total protein extracts were prepared from cell cultures using a sintered glass tissue homogenizer (Wheaton, Millville, N.J., USA) in phosphate-buffered saline (PBS), pH 7.5, 3M urea. For detection of β-catenin, cell cultures were washed with PBS, trypsinized, and pelleted at 1,000 rpm for 4 minutes. The cell pellets were washed and resuspended in cold hypotonic buffer consisting of 10 mM HEPES (pH 7.5), 1.5 mM $MgCl_2$, 10 mM KCl, 0.5 mM DTT, and EDTA-free protease inhibitor (Roche, Laval, QC, Canada) in an ice bath for 5 minutes. The mixture was then homogenized using a dounce homogenizer and the cellular debris was pelleted by centrifugation at 4° C. Cytoplasmic fractions were recovered and used for assaying β-catenin.

Protein concentrations were determined by the Peterson method (Peterson, Analyt. Biochem., 83: 346-356, 1977). Proteins (20 μg/lane) were loaded onto SDS-polyacrylamide gels and separated by electrophoresis. Proteins in gels were transferred onto PVDF membranes and processed for antibody reactions. To detect CREB, S133-phosphorylated CREB, and GAPDH loading controls, antibodies were diluted in 2% ECL Advance™ blocking reagent (GE Healthcare, Mississauga, ON, Canada) and solubilized in PBS-Tween20. Membranes were probed overnight at 4° C. Membranes were washed four times with PBS-Tween20 and labeled for 1 hour at 20° C. with secondary antibodies conjugated to horseradish peroxidase (HRP). The membrane was washed four more times with PBS-Tween20 and HRP activity was developed using Advance™ chemiluminescence (ECL) reagent (GE Healthcare, Mississauga, ON, Canada) according to the manufacturer's instructions. PVDF membranes were exposed to X-ray film.

Immuno-Slotblot Assay for Secreted BDNF in Cell Culture Media

Cell culture media from cells that were not treated or treated with DMSO, 1, 5 or 10 μM latanoprost treated was collected in 15-mL screw cap polypropylene tubes from cell culture dishes. Cellular debris from cultures were pelleted by centrifugation at 2000 rpm for 5 minutes at 4° C. using a clinical centrifuge. The relative amount of BDNF secreted by U87MG astrocytoma and MO3-13 oligodendrocyte cell lines were determined by an immune-slotblot method in which 200 μL of conditioned media was applied in triplicate to nitrocellulose membrane pre-wet in water in a Biodot (SF) ultrafiltration unit (Bio-Rad Laboratories, Mississauga, ON, Canada) under vacuum. Each sample was applied onto wetted nitrocellulose membrane. Nitrocellulose membrane containing filtration retentate was blocked with a solution of 2% Advance ECL blocking solution (GE Healthcare) solubilized in phosphate buffered saline containing 0.01% Tween 20 (PBST) for one hour at room temperature. The membrane was incubated overnight at 4° C. with the primary anti-BDNF antibody (Abcam, Cambridge, Mass.) in blocking solution, then washed three times with PBST (15 minutes each). Secondary IgG conjugated with horseradish peroxidase (HRP) diluted in blocking solution was added to the membrane and incubated at room temperature for one hour. After washing the membrane as above, the bound secondary antibody was detected by ECL Advance™ Western blot HRP substrate (GE Healthcare) using a ChemiDoc™ MP Imaging System (Bio-Rad Laboratories). The relative amount of BDNF was determined by using ImageLab™ software (BioRad). Statistical significance between means was assessed by student t-tests. Statistical significance was set at 5%, with error bars showing a single standard deviation.

Mouse Strains and Housing

DBA/2J strain mice (Jackson Laboratories, Bar Harbor, Me., USA) were obtained with an approximate starting age of 8 weeks and an average body weight of 25.9 g. Mice were acclimatized for at least three days prior to study commencement, and animals in poor condition were rejected during the acclimatization period. All mice were housed under identical conditions in animal rooms with HEPA-filtered air at a temperature of 70° F.+/−5° F. and a relative humidity of 50%+/−20%. Animal rooms maintained a minimum of 12 to 15 air changes per hour with a light/dark cycle of 12 hours on and 12 hours off with no twilight. Sterile Bed-O-Cobs® bedding was used and changed a minimum of once per week. All animals were fed a sterile Purina Labdiet® 5053 rodent diet and water was provided ad libitum.

Open Field Test

At the commencement of the study, sixty (60) mice were randomly divided into six (6) groups of ten (10) animals. Each animal was identified by a marking on the tail of the mouse. Prior to the onset of the test session, mice were administered latanoprost, amphetamine, lithium, or saline as outlined in Table 1. All drug solutions were administered as a single acute dose. Drug solutions were prepared in sterile saline (0.9%) and administered via the intraperitoneal (IP) cavity in a volume of 5 mL/kg. Mice were then exposed to a single 20-minute session in an open field chamber (22×22×15 cm), which was lit with diffuse white light. During this time, distance traveled was automatically recorded using TopScan (Clever Sys, Reston, Va., USA) video tracking software.

TABLE 1

| Group Number | Number of Animals | Treatment | Dosage | Dosing Schedule |
| --- | --- | --- | --- | --- |
| 1 | 10 | Saline-Vehicle | n.a.-n.a. | Immediately prior to test-1 hour prior to test |
| 2 | 10 | Saline-Latanoprost | n.a.-40 mg/kg | Immediately prior to test-1 hour prior to test |
| 3 | 10 | Saline-Lithium | n.a.-200 mg/kg | Immediately prior to test-1 hour prior to test |
| 4 | 10 | Amphetamine-Vehicle | 0.5 mg/kg-n.a. | Immediately prior to test-1 hour prior to test |
| 5 | 10 | Amphetamine-Latanoprost | 0.5 mg/kg-40 mg/kg | Immediately prior to test-1 hour prior to test |
| 6 | 10 | Amphetamine-Lithium | 0.5 mg/kg-200 mg/kg | Immediately prior to test-1 hour prior to test | n.a. = not applicable

Example 2

Effect of Latanoprost and Other Prostaglandin (PG) Derivatives on Glycogen Synthase Kinase-3 (GSK-3) Activity Distalless LacZ Expression in *Drosophila* Wing Imaginal Discs Using *Drosophila*, GSK-3 function was assayed unequivocally and with high specificity in vivo using the transcription of the Wnt/Wg target gene Distalless (Dll) in the developing wing tissue. GSK-3 is required for the inhibition of Dll in this tissue. Loss of GSK-3 activity leads to ectopic Dll expression.

Figure 1B:
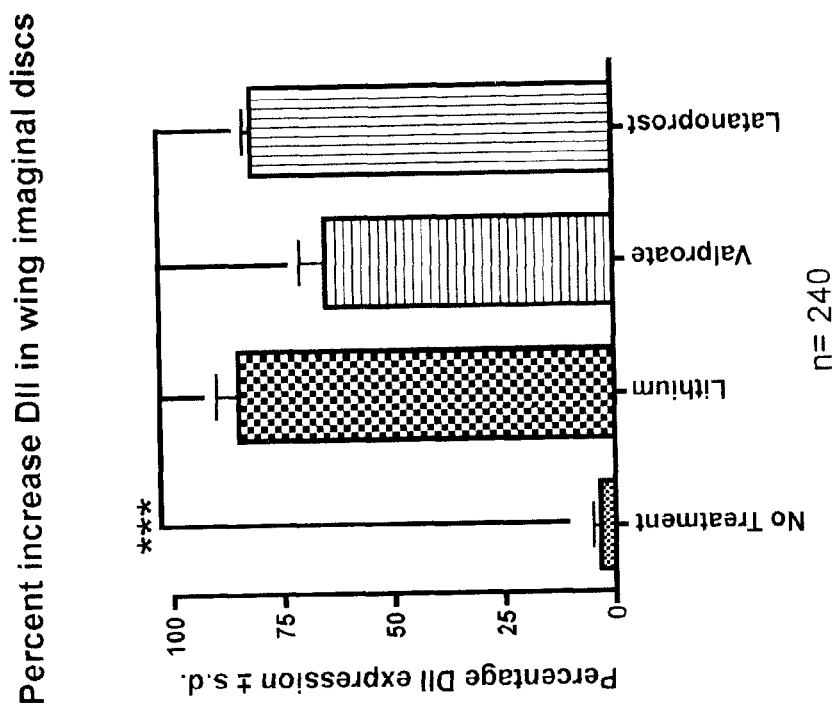
FIG. 1B is a graph showing the mean percent increase in Dll expression in wing imaginal discs. n=240, error bars represent the standard deviation from the mean, *** indicates p-value<0.001.
Figure 2A:
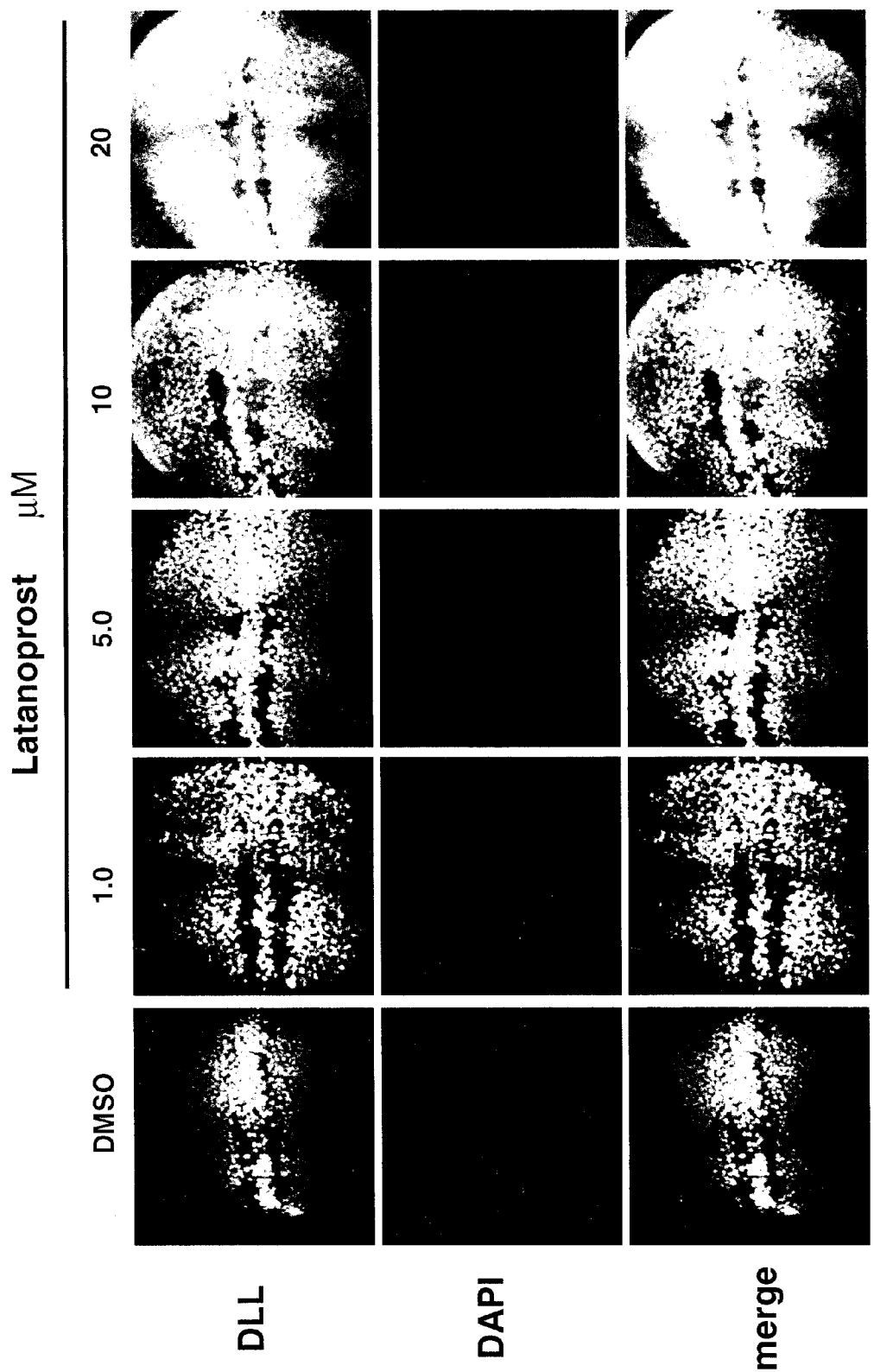
FIG. 2A is a series of confocal microscope images of *Drosophila* wing imaginal discs showing the effect of latanoprost on Distalless protein (DLL) levels in the wing pouch. DAPI labeled nuclei. Merged DAPI and DLL channels are shown on the bottom row.
Figure 2B:
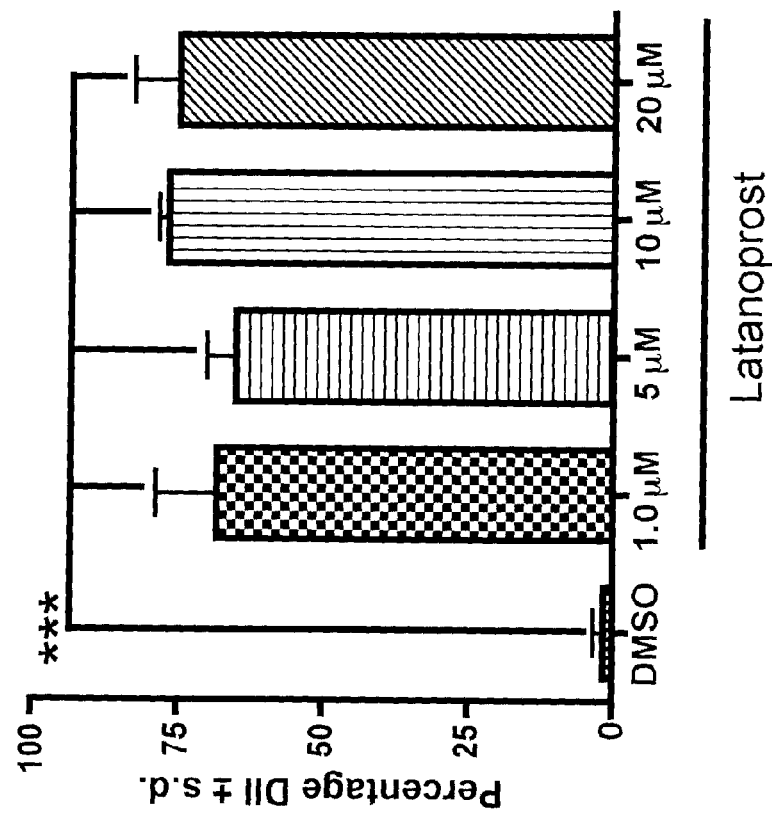
FIG. 2B is a graph showing the mean percent increase in Dll expression in wing imaginal discs. n=300, error bars represent the standard deviation from the mean, *** indicates p-value<0.001.
Figure 3A:
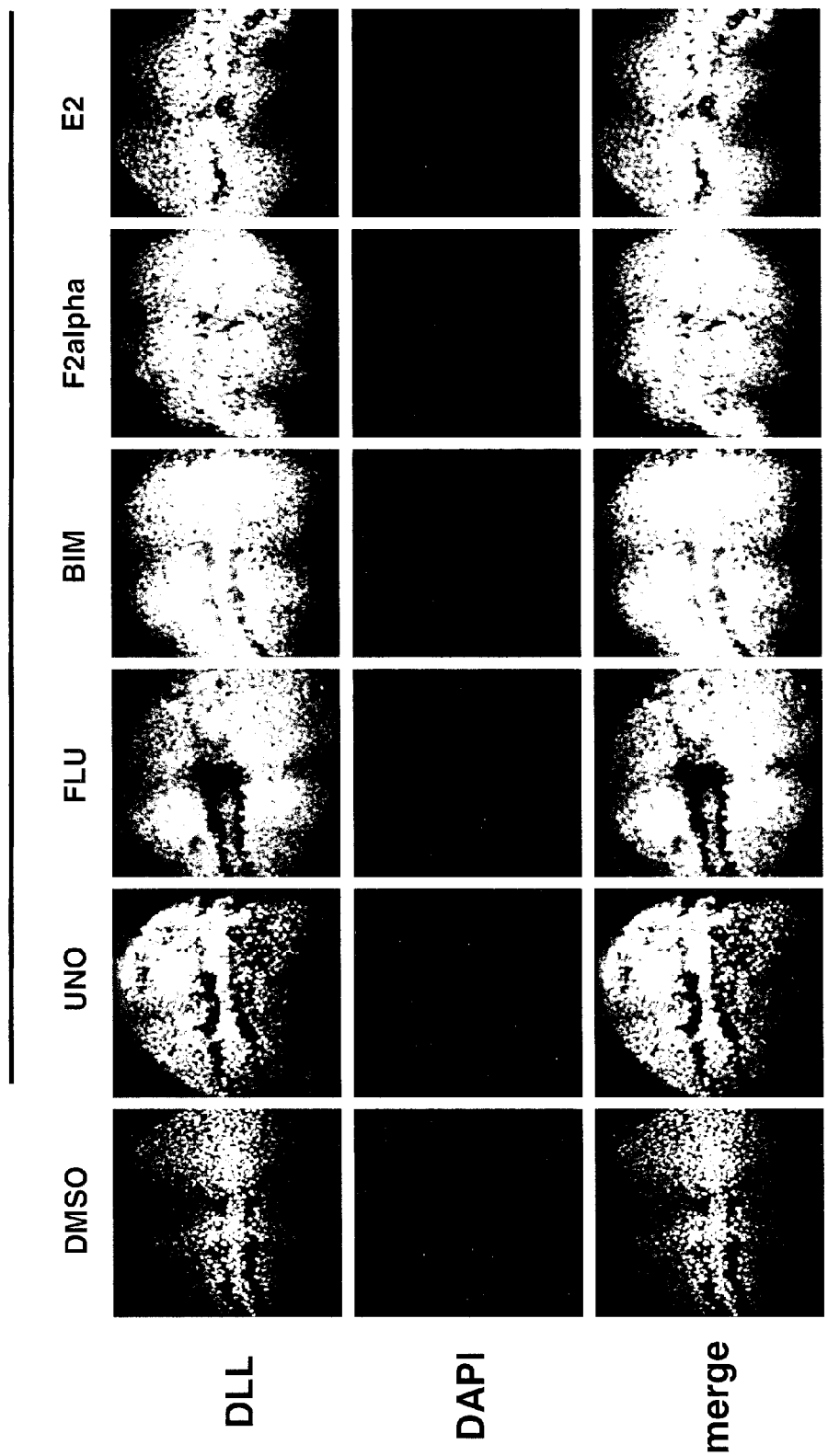
FIG. 3A is a series of confocal microscope images of *Drosophila* wing imaginal discs showing the effect of latanoprost-like molecules on Distalless protein (DLL) levels in the wing pouch. DAPI labeled nuclei. Merged DAPI and DLL channels are shown on the bottom row. DMSO was the vehicle for the test compounds. UNO=unoprostone, BIM=bimatoprost, FLU=fluprostenol, F2alpha=Prostaglandin F2α/PGF2α, E2=Prostaglandin E2/PGE2.
Figure 3B:
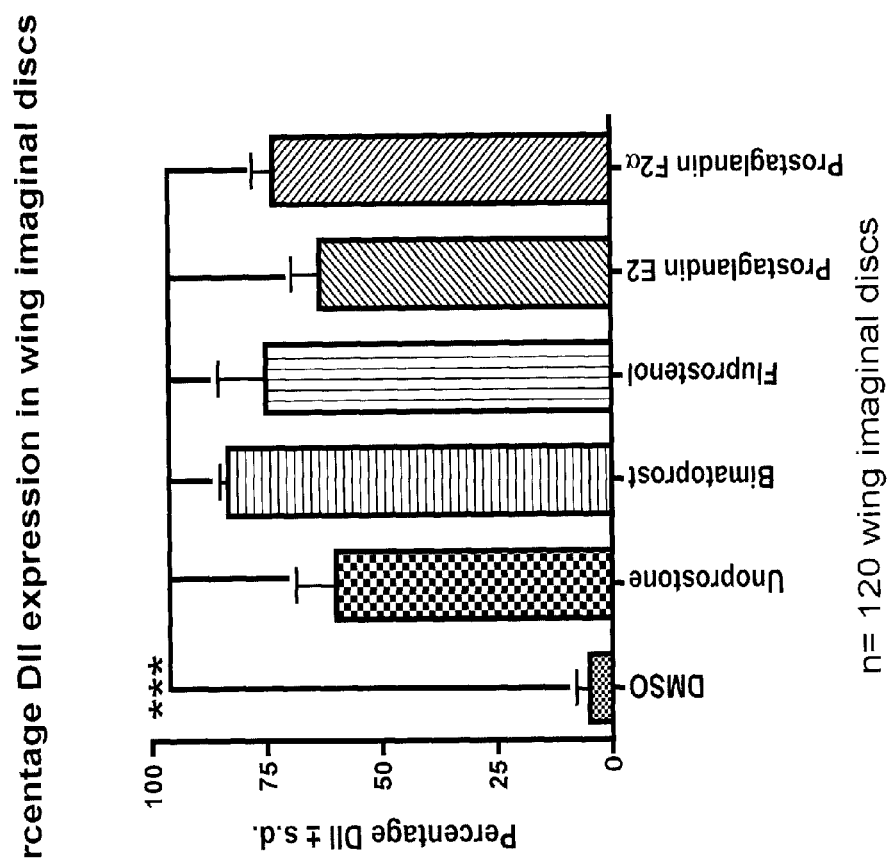
FIG. 3B is a graph showing the mean percent increase in Dll expression in wing imaginal discs. n=120, error bars represent the standard deviation from the mean, *** indicates p-value<0.001.

We first used this assay to test the effects of latanoprost compared with two known drugs (lithium and valproate) for the treatment of neuropsychiatric disorders such as bipolar disorder. Whereas DMSO treatment of imaginal discs from "wild-type" (i.e., non-mutant) normal third instar larvae revealed minimal effects on Dll expression, treatment of discs with either 1 mM lithium or 1 mM valproate resulted in the activation of Dll expression (FIGS. 1A and 1B). Latanoprost (20 µM) also resulted in increased Dll expression (FIGS. 1A and 1B), indicating that similar to lithium and valproate, latanoprost also inhibited GSK-3 signaling. Using this assay, we found that treatment of wing imaginal discs with increasing doses (1 µM, 5 µM, 10 µM, and 20 µM) of the prostaglandin F2α derivative, latanoprost, all resulted in a significant activation of Dll and thus inhibition of GSK-3 activity in vivo compared to treatment with a DMSO control vehicle (FIGS. 2A and 2B). We next confirmed that other prostaglandin (PG) and PG derivatives (unoprostone, fluprostenol, bimatoprost, prostaglandin F2-α, and prostaglandin E2) exhibit a similar significant effect to that of latanoprost (FIGS. 3A and 3B). In these experiments, wing imaginal discs were treated with 1 µM PG or PG derivative (e.g., unoprostone, bimatoprost, fluprostenol) over 12 hours. Together, these data show that, similar to lithium and valproate, PG and PG derivatives inhibit GSK-3 in vivo.

Glycogen Deposition in Fat Body Tissue

Figure 4:
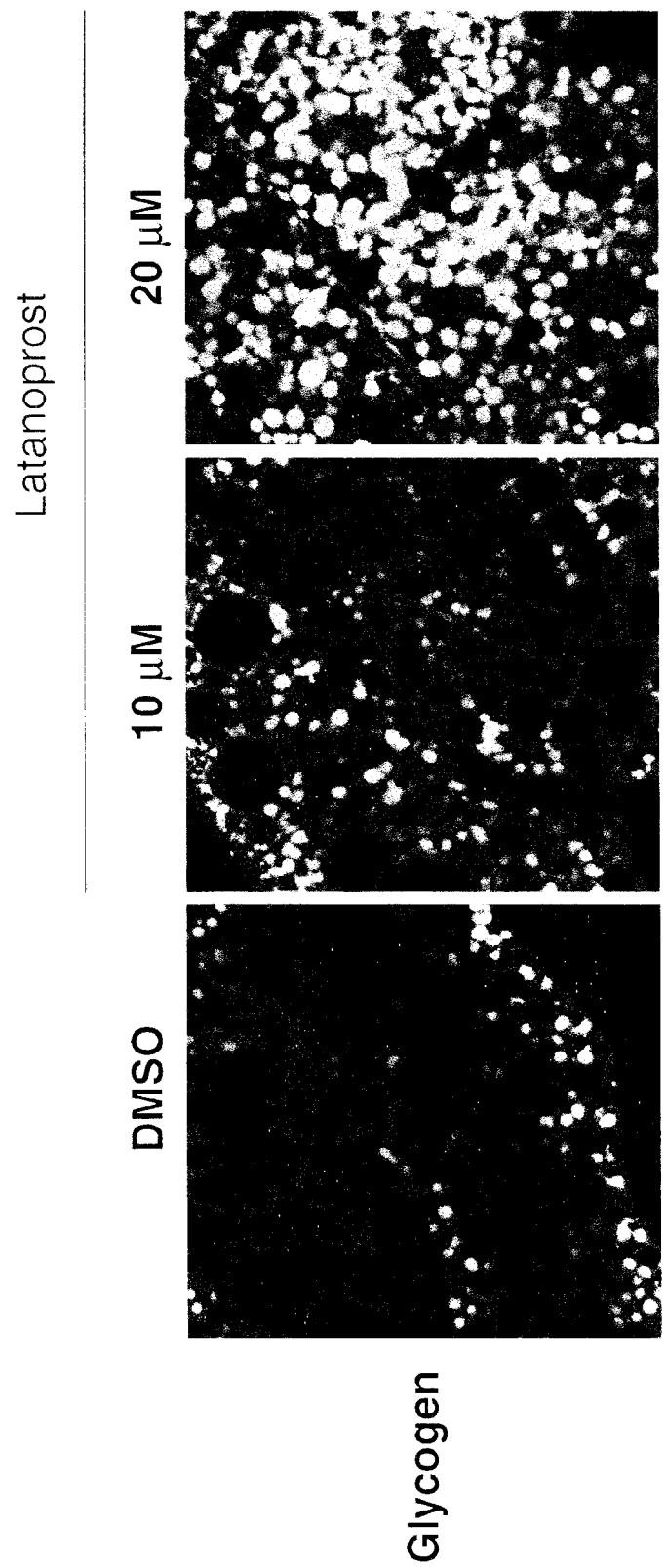
FIG. 4 is a series of images showing that latanoprost treatment results in glycogen accumulation in *Drosophila melanogaster* fat body tissue from third instar larvae.

GSK-3 also functions in glycogen deposition via an independent pathway to that of the Wnt/Wg signaling pathway. GSK-3 functions in the glycogen deposition pathway by phosphorylating and inactivating glycogen synthase, which catalyzes the rate-limiting step of glycogen synthesis. To further confirm that PG and PG derivatives inhibit GSK-3 activity, fat body tissue from third instar *Drosophila melanogaster* larvae was treated with vehicle (DMSO) or 10 and 20 µM latanoprost and the effects of drug treatment on glycogen accumulation was monitored. Treatment of fat body tissue with latanoprost resulted in an increase in glycogen accumulation in a dosage-dependent manner, consistent with latanoprost inhibiting GSK-3 activity (FIG. 4).

Figure 5:
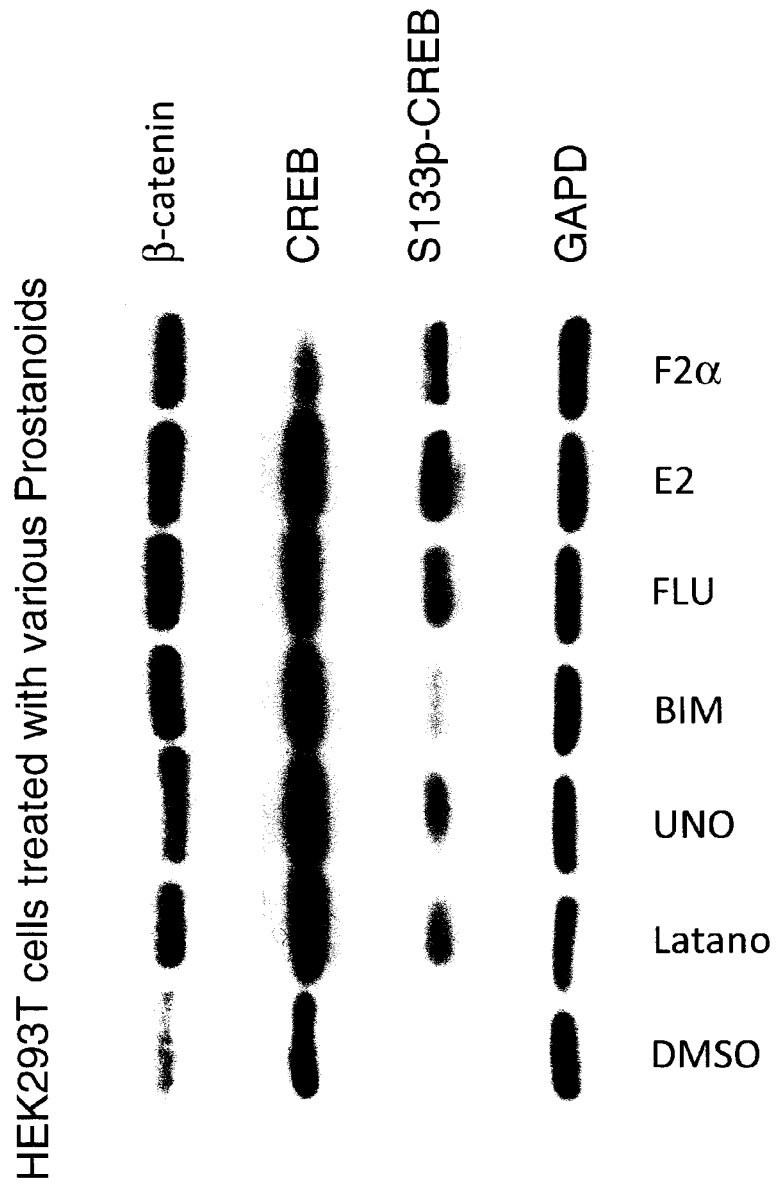
FIG. 5 is a series of Western immunoblot images showing cytoplasmic β-catenin levels, CREB transcription factor levels, and Serine-133 (S133) phosphorylated CREB transcription factor levels in HEK293T cells treated with latanoprost or latanoprost-like molecules. Anti-β-catenin antibody was used to detect β-catenin. Anti-CREB and anti-S133 phosphorylated CREB antibodies were used to detect CREB and S133 CREB, respectively. Anti-GAPD antibody was used as a loading control. DMSO was the vehicle for the test compounds. UNO=unoprostone, BIM=bimatoprost, FLU=fluprostenol, F2alpha=Prostaglandin F2α/PGF2α, E2=Prostaglandin E2/PGE2.

Example 3

β-Catenin Stabilization and CREB Transcription Factor Activation by PG and PG Derivatives β-Catenin Stabilization To confirm the GSK-3 inhibition results in mammalian cells, HEK293T cells were treated with DMSO vehicle, 10 µM PG (e.g., PGF2α, PGE2), or 10 µM PG derivative (e.g., latanoprost). Western blot analysis of protein extracts from the PG or PG derivative-treated cells showed increased levels of cytoplasmic β-catenin compared to that from DMSO-treated cells (FIG. 5). When phosphorylated by GSK-3, cytoplasmic β-catenin levels are low due to proteosome-mediated degradation. Therefore, basal levels of cytoplasmic β-catenin are low. PG and PG derivatives stabilize the levels of cytoplasmic 0-catenin, indicating that these compounds also inhibit GSK-3 in mammalian cells.

CREB Transcription Factor Activation

A number of neuropsychiatric conditions are treated by mood stabilizers and antidepressants, which regulate a number of pathways involved in cell survival (e.g., by activation of the CREB transcription factor). CREB is activated by phosphorylation at S133, enabling interaction with CREB binding protein and regulation of gene expression. Therefore, CREB phosphorylation can be considered a relevant clinical surrogate for neuropsychiatric conditions such as bipolar disease.

To test the efficacy of latanoprost and other PG or PG derivatives for CREB activation, HEK293T cells were treated with PG or PG derivatives (10 µM), or DMSO. Western blot analysis of protein extracts from the PG or PG derivative-treated cells showed increased levels of S133 phosphorylated-CREB compared to that from DMSO-treated cells (FIG. 5), indicative of the downstream effects of CREB activation via phosphorylation at residue S133.

Example 4

Effect of Latanoprost on Brain-derived Neurotrophic Factor (BDNF) Levels in Human Astrocyte and Oligodendrocyte Cell Lines Brain-derived neurotrophic factor (BDNF), a member of the growth factor family, may be important in contributing to changes in neuroplasticity in connection with neuropsychiatric conditions (e.g., bipolar disorder). In particular, subjects with bipolar disorder have been found to have decreased levels of BDNF in their serum during depressive and/or manic episodes, with BDNF levels returning to normal in euthymia (de Oliveira, G. S., Cereser, K. M., Fernandes, B. S., Kauer-Sant'Anna, M., Fries, G. R., Stertz, L., Aguiar, B., Pfaffenseller, B., and Kapczinski, F. J., Psychiatr Res., 43: 1171-1174, 2009; Tramontina, J. F., Andreazza, A. C., Kauer-Sant'anna, M., Stertz, L., Goi, J., Chiarani, F., and Kapczinski, F., Neurosci Lett., 452: 111-113, 2009; Lin, P. Y., Neurosci Lett., 466: 139-143, 2009; Fernandes, B. S., Gama, C. S., Cereser, K. M., Yatham, L. N., Fries, G. R., Colpo, G., de Lucena, D., Kunz, M., Gomes, F. A., and Kapczinski, F., J. Psychiatr. Res. 45: 995-1004, 2011).

Figure 6:
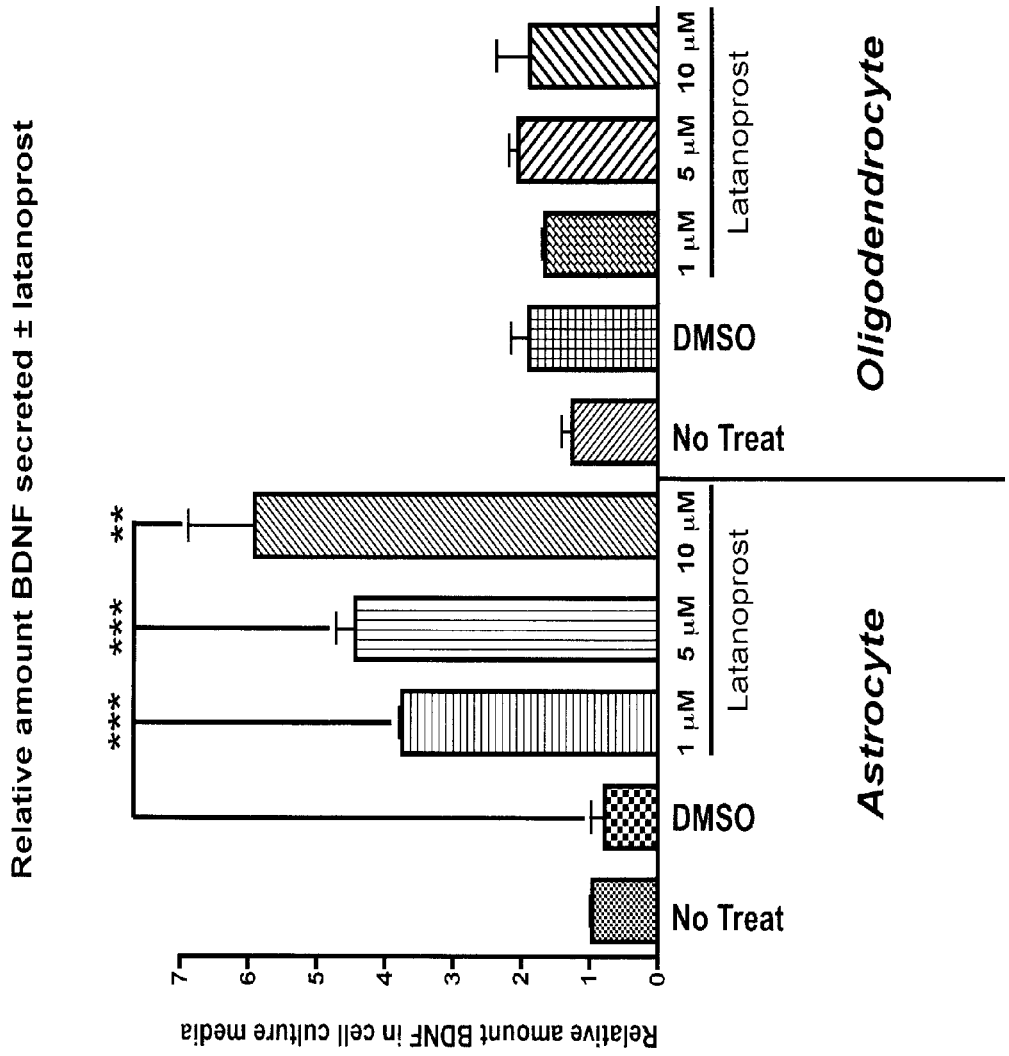
FIG. 6 is a graph showing the mean relative amounts of brain-derived neurotrophic factor (BDNF) secreted by human astrocytoma and oligodendrocytes cell lines not treated (No Treat), treated with DMSO vehicle, or treated with latanoprost (1 µM, 5 µM, 10 µM). n=3, error bars represent the standard deviation from the mean,  represents p<0.007, * represents p<0.0004.

To test the effect of PG or PG derivatives on BDNF secretion, the conditioned media from human astrocytoma and human oligodendrocyte cell lines were assayed for secreted BDNF upon treatment with latanoprost at various doses (1 µM, 5 µM, 10 µM). The relative amount of BDNF was compared with the amount of BDNF secreted by non-treated cells and cells treated with DMSO vehicle. The amount of BDNF secreted increased significantly in astrocyte conditioned media, whereas in the oligodendrocytes media no significant increase in BDNF levels was detected (FIG. 6). These data indicate that astrocytes, but not oligodendrocytes, secrete BDNF in response to latanoprost treatment. Whereas PG or PG derivatives like latanoprost regulate BDNF secretion (Toyomoto, M., Ohta, M., Okumura, K., Yano, H., Matsumoto, K., Inoue, S., Hayashi, K., and Ikeda, K., FEBS Lett., 562: 211-215, 2004), lithium is not effective in regulating BDNF levels and/or activity. Therefore, PG or PG derivatives like latanoprost may exhibit a wider spectrum of activity compared to the classical bipolar disorder treatment of lithium.

Example 5

Effects of Latanoprost on Other Bipolar Disorder Biomarkers

Figure 7:
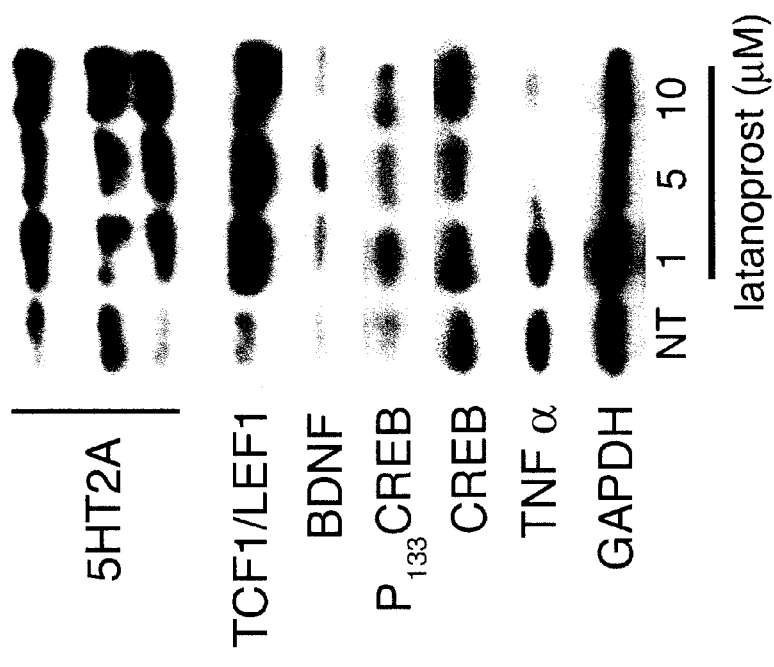
FIG. 7 is a series of Western blot images showing the relative levels of 5HT2A, TCF1/LEF1, BDNF, phosphorylated Ser133-CREB, CREB, and TNF-α in U87MG cells following no treatment (NT) or treatment with latanoprost (1 μM, 5 μM, 10 μM). GAPDH was used as a loading control.

We next examined the effects of latanoprost treatment (1 µM, 5 µM, and 10 µM) on other bipolar disorder biomarkers in glioblastoma U87 cell line. Compared to untreated cells, latanoprost-treated cells were found to have increased levels of the serotonin receptor 5HT2A, the transcription factor TCF/LEF1, BDNF, and phosphorylation at Ser133 on CREB despite the total level of CREB protein remaining relatively constant (FIG. 7). Treatment of U87 cells with latanoprost also resulted in reduced levels of the inflammatory cytokine TNF-α (FIG. 7). These results indicate that glioblastoma cells treated with latanoprost share many response phenotypes to that of cells treated with lithium.

Example 6

In Vivo Effect of Latanoprost in the Amphetamine-Stimulated Activity Mouse Model of Bipolar Disorder The data herein indicate that PG and PG derivatives may be effective in treating neuropsychiatric conditions such as bipolar disorder. Therefore, we evaluated the efficacy of latanoprost in an open field model of bipolar disorder in mice. DBA/2J mice were divided into six groups of ten animals. Mice were treated with vehicle, latanoprost (40 mg/kg), or lithium (6 mg/kg) one hour prior to testing Immediately prior to placement in the open field chamber, the groups were administered either 0.5 mg/kg amphetamine or saline as described in Table 1.

Figure 8:
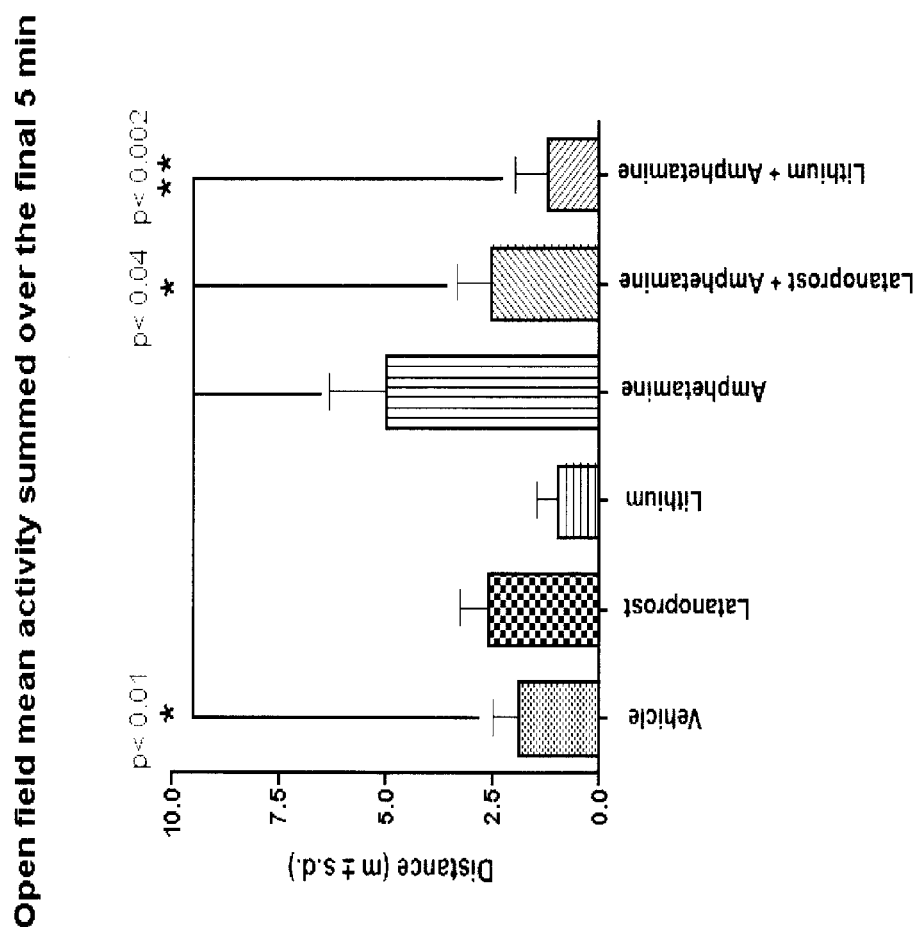
FIG. 8 is a graph showing that latanoprost significantly (P<0.05) attenuates amphetamine (AMPH)-induced hyperlocomotion of mice in an open field study. The mean distance traveled for each test group was summed over the final five minutes of a 20-minute test, when AMPH-induced stimulation of activity was greatest. n=10 mice/test group. Error bars represent standard error of the mean (SEM). * represents p<0.05. ** represents p<0.005.

Total distance traveled for each mouse over a 20-minute session was recorded using TopScan (Clever Sys, Reston, Va., USA) video tracking software. In the final five (5) minutes of the open field test, when the effect of amphetamine was greatest, latanoprost significantly reduced the amphetamine-stimulated locomotion (FIG. 8). Group differences were assessed using Two-Way ANOVA with dose 1 (vehicle, latanoprost, or lithium) and dose 2 (saline or amphetamine) as factors. Two-Way ANOVA analysis revealed a significant main effect of dose 1 ($F2,54=4.1$; $P=0.022$) and a non-significant trend for amphetamine administration ($F1,54=2.6$; $P=0.115$). An interaction of dose 1 and dose 2 ($F2,54=2.2$; $P=0.122$) was also observed. Given the significant effect of dose 1 and a trend in both dose 2 and the interaction of the two doses, post hoc analysis was performed using the Holm-Sidak method to compare treatment versus control groups. Significantly greater activity was observed in mice that received vehicle and amphetamine than vehicle and saline ($P=0.011$), latanoprost and amphetamine ($P=0.042$), or lithium and amphetamine ($P=0.002$) (FIG. 8). No significant differences in activity were observed in saline-treated mice that received vehicle, latanoprost, or lithium.

Example 7

β-Catenin Stabilization in the Brain of Latanoprost-Treated Mice

Figure 9:
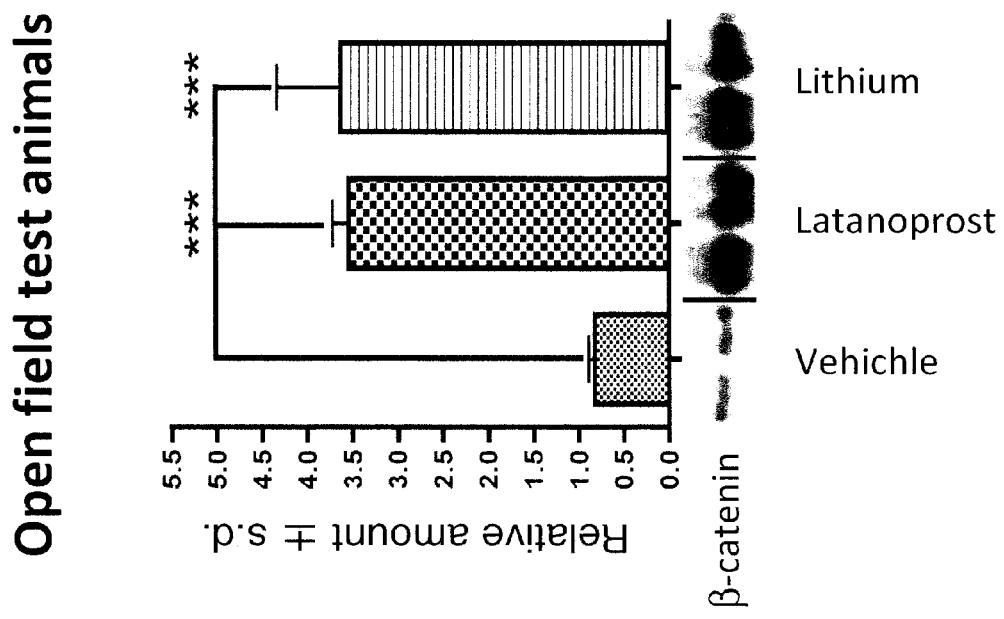
FIG. 9 is a graph and images showing indicating the level of β-catenin stabilization in open field test mice treated with vehicle (DMSO), latanoprost, or lithium. The graph (top) represents the mean relative amount of β-catenin (n=3). The error bars represent the standard deviation from the mean. *** represents p<0.001. The images (bottom) show representative anti-β-catenin Western blots of two individuals per group.

Following the open field test behavioral analysis of mice, the mice were euthanized and their brains were dissected and bifurcated along the longitudinal fissure. Brain samples from mice treated with vehicle (saline), latanoprost, or lithium were processed for β-catenin stabilization by extraction with hypotonic buffer. The levels of stabilized β-catenin were analyzed by Western blot, and the relative amounts of β-catenin (represented as the mean relative amount of three mice per group) were quantified. Both latanoprost- and lithium-treated mice had significantly increased levels of β-catenin relative to mice treated with saline (FIG. 9), suggesting bioavailability in the brain.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth.

All publications and patent applications mentioned in this specification are herein incorporated by reference to the same extent as if each independent publication or patent application was specifically and individually indicated as being incorporated by reference in their entirety.

What is claimed is:

1. A method of ameliorating or palliating a subject having bipolar disorder, the method comprising administering to the subject a therapeutically effective amount of a pharmaceutical composition comprising latanoprost, travoprost or bimatoprost, or a prodrug thereof, or a pharmaceutically acceptable salt thereof.

2. The method of claim 1, wherein the latanoprost, travoprost or bimatoprost, or a prodrug thereof, or a pharmaceutically acceptable salt thereof, is administered in an amount sufficient to inhibit glycogen synthase kinase-3 (GSK-3) in the subject.

3. The method of claim 2, wherein the latanoprost, travoprost or bimatoprost, or a prodrug thereof, or a pharmaceutically acceptable salt thereof, is administered in an amount sufficient to produce a steady state plasma concentration of from about 1 pg/ml to about 10 ng/ml.

4. The method of claim 1, wherein the latanoprost, travoprost or bimatoprost, or a prodrug thereof, or a pharmaceutically acceptable salt thereof, is deuterium-enriched and/or nitrosylated.

5. The method of claim 1, wherein the latanoprost, travoprost or bimatoprost, or a prodrug thereof, or a pharmaceutically acceptable salt thereof is present in the pharmaceutical composition at a concentration of from about 0.00001% to about 0.2% (w/v).

6. The method of claim 1, wherein the subject is a human.

7. The method of claim 1, wherein the pharmaceutical composition is administered intramuscularly, intravenously, intradermally, intraarterially, intraperitoneally, intranasally, intravitreally, intrarectally, subcutaneously, subconjunctivally, intravesicularly, mucosally, intraocularally, orally or topically; or by inhalation, infusion, continuous infusion, or in cremes or lipid compositions.

8. The method of claim 1, wherein the pharmaceutical composition comprises a pharmaceutically acceptable carrier.

9. The method of claim 1, wherein the bipolar disorder is bipolar I disorder, bipolar II disorder, cyclothymia, mixed bipolar disorder, rapid-cycling bipolar disorder, hypomania, dysthymia, or acute mania.

10. The method of claim 3, wherein the steady state plasma concentration of latanoprost, travoprost or bimatoprost, or a prodrug thereof, or a pharmaceutically acceptable salt thereof, is from about 1 pg/ml to about 500 pg/ml.

11. The method of claim 3, wherein the steady state plasma concentration of latanoprost, travoprost or bimatoprost, or a prodrug thereof, or a pharmaceutically acceptable salt thereof, is from about 500 pg/ml to about 1 ng/ml.

12. The method of claim 3, wherein the steady state plasma concentration of latanoprost, travoprost or bimatoprost, or a prodrug thereof, or a pharmaceutically acceptable salt thereof, is from about 1 ng/ml to about 10 ng/ml.

13. The method of claim 5, wherein the latanoprost, travoprost or bimatoprost, or a prodrug thereof, or a pharmaceutically acceptable salt thereof, is present in the pharmaceutical composition at a concentration of from about 0.001% to about 0.2% (w/v).

14. The method of claim 13, wherein the latanoprost, travoprost or bimatoprost, or a prodrug thereof, or a pharmaceutically acceptable salt thereof, is present in the pharmaceutical composition at a concentration of from about 0.001% to about 0.02% (w/v).

* * * * *

UNITED STATES PATENT AND TRADEMARK OFFICE
CERTIFICATE OF CORRECTION

PATENT NO. : 9,259,409 B2  
APPLICATION NO. : 13/981360  
DATED : February 16, 2016  
INVENTOR(S) : Fabrizio G. Mastronardi Page 1 of 1

It is certified that error appears in the above-identified patent and that said Letters Patent is hereby corrected as shown below:

In the claims,
Column 22, Claim 7, Line 6, replace "intraocularally" with --intraocularly--.

Signed and Sealed this
Thirty-first Day of May, 2016

Michelle K. Lee
*Director of the United States Patent and Trademark Office*